(12) United States Patent
Shirley

(10) Patent No.: US 11,781,855 B2
(45) Date of Patent: Oct. 10, 2023

(54) SURFACE SENSING PROBE AND METHODS OF USE

(71) Applicant: Lyle G. Shirley, Boxborough, MA (US)

(72) Inventor: Lyle G. Shirley, Boxborough, MA (US)

(*) Notice: Subject to any disclaimer, the term of this patent is extended or adjusted under 35 U.S.C. 154(b) by 0 days.

(21) Appl. No.: 17/186,860

(22) Filed: Feb. 26, 2021

(65) Prior Publication Data

US 2021/0356250 A1 Nov. 18, 2021

Related U.S. Application Data

(63) Continuation of application No. 16/357,263, filed on Mar. 18, 2019, now Pat. No. 10,935,364, which is a (Continued)

(51) Int. Cl.
*G01B 11/02* (2006.01)
*G01B 9/02004* (2022.01)
(Continued)

(52) U.S. Cl.
CPC .......... *G01B 9/02004* (2013.01); *A61B 5/117* (2013.01); *G01B 9/02005* (2013.01); (Continued)

(58) Field of Classification Search
CPC ............ G01B 9/02094; G01B 9/02095; G01B 9/02096; G01B 9/02019; G01B 2290/30; (Continued)

(56) References Cited

U.S. PATENT DOCUMENTS

| 6,424,407 B1* | 7/2002 | Kinrot | G01D 5/347 356/28 |
| 2007/0139381 A1* | 6/2007 | Spurlock | G06F 3/0317 345/166 |
| 2011/0013198 A1* | 1/2011 | Shirley | G01B 11/25 356/610 |

FOREIGN PATENT DOCUMENTS

GB 0024167 A2 * 2/1981

OTHER PUBLICATIONS

Katherine Creath, "Phase-shifting speckle interferometry," Appl. Opt. 24, 3053-3058 (1985) (Year: 1985).*

(Continued)

*Primary Examiner* — Uzma Alam
*Assistant Examiner* — Jonathon Cook
(74) *Attorney, Agent, or Firm* — John Brooks Law LLC; John J. Brooks, III

(57) ABSTRACT

Disclosed is a surface sensing apparatus, one embodiment having a source of coherent radiation capable of outputting wavelength emissions to create a first illumination state to illuminate a surface and create a first speckle pattern, an emission deviation facility capable of influencing the emission to illuminate the surface and create a second illumination state and a second speckle pattern, and a sensor capable of sensing a representation of the first and a second speckle intensity from the first and second speckle pattern. Also disclosed are methods of sensing properties of the surface, one embodiment comprising the steps of illuminating the surface having a first surface state with the source of coherent radiation emission, sensing a first speckle intensity from the surface, influencing a relationship of the surface to the emission to create a second surface state and sensing a second speckle intensity from the surface at the second surface state.

11 Claims, 11 Drawing Sheets

Related U.S. Application Data continuation of application No. 15/420,555, filed on Jan. 31, 2017, now Pat. No. 10,281,257, which is a continuation of application No. 14/281,255, filed on May 19, 2014, now Pat. No. 9,582,883, which is a continuation-in-part of application No. 13/568,229, filed on Aug. 7, 2012, now Pat. No. 8,761,494, and a continuation-in-part of application No. 13/189,349, filed on Jul. 22, 2011, now Pat. No. 8,736,847, and a continuation-in-part of application No. 12/921,185, filed as application No. PCT/US2009/037999 on Mar. 23, 2009, now Pat. No. 8,810,800.

(60) Provisional application No. 61/435,283, filed on Jan. 22, 2011, provisional application No. 61/367,409, filed on Jul. 24, 2010, provisional application No. 61/115,923, filed on Nov. 18, 2008, provisional application No. 61/070,352, filed on Mar. 22, 2008.

(51) Int. Cl.
| | |
|---|---|
| *A61B 5/117* | (2016.01) |
| *G06F 21/32* | (2013.01) |
| *G06T 7/55* | (2017.01) |
| *G01B 9/02055* | (2022.01) |
| *G01B 9/02* | (2022.01) |
| *G01B 11/24* | (2006.01) |
| *G01B 9/02002* | (2022.01) |
| *G06T 7/521* | (2017.01) |
| *G01B 11/14* | (2006.01) |
| *G06V 10/143* | (2022.01) |
| *G06F 18/25* | (2023.01) |
| *G06V 10/80* | (2022.01) |
| *A61B 5/00* | (2006.01) |

(52) U.S. Cl.
CPC ..... *G01B 9/02069* (2013.01); *G01B 9/02083* (2013.01); *G01B 9/02094* (2013.01); *G01B 9/02096* (2013.01); *G01B 11/14* (2013.01); *G01B 11/2441* (2013.01); *G06F 18/253* (2023.01); *G06F 21/32* (2013.01); *G06T 7/521* (2017.01); *G06T 7/55* (2017.01); *G06V 10/143* (2022.01); *G06V 10/806* (2022.01); *A61B 5/0077* (2013.01); *A61B 2576/00* (2013.01); *G06T 2207/10152* (2013.01)

(58) Field of Classification Search
CPC ... G01B 11/2441; G01B 11/162; G01D 5/266
See application file for complete search history.

(56) References Cited

OTHER PUBLICATIONS

Zizka, Jan & Olwal, Alex & Raskar, Ramesh. (2011). SpeckleSense: Fast, precise, low-cost and compact motion sensing using laser speckle. UIST'11—Proceedings of the 24th Annual ACM Symposium on User Interface Software and Technology. 489-498. 10.1145/2047196.2047261. (Year: 2011).*

* cited by examiner

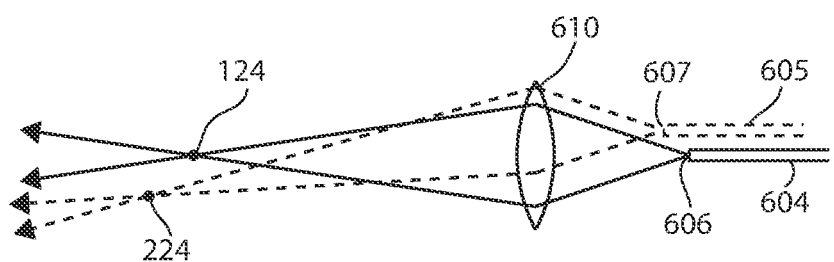
FIG. 7A
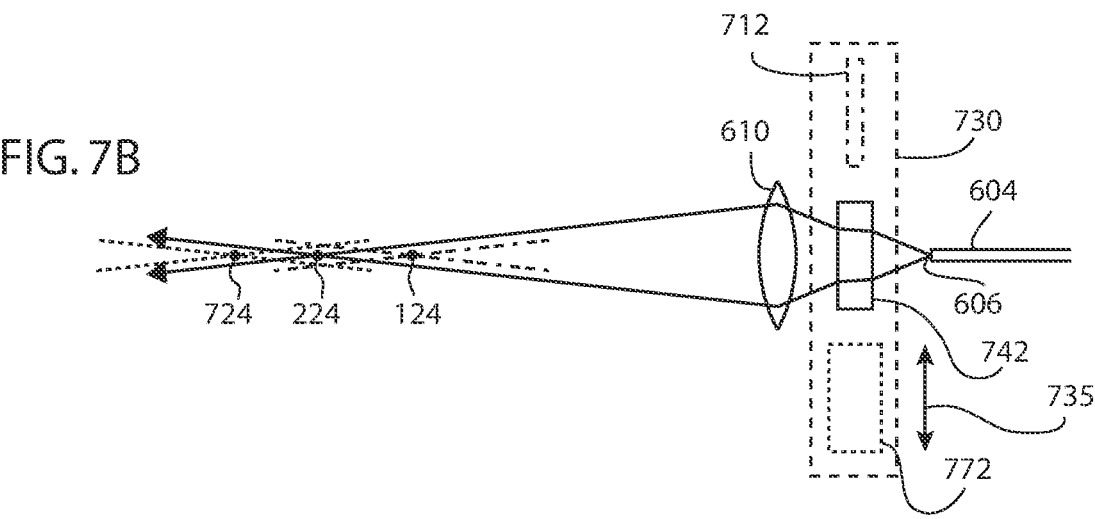
FIG. 7B
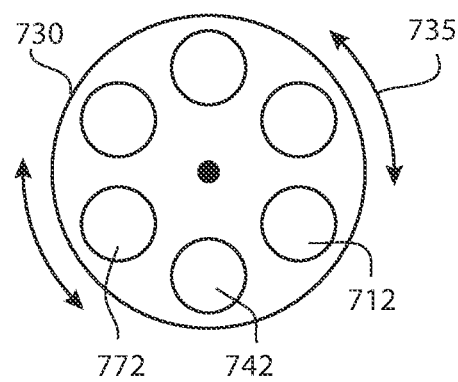

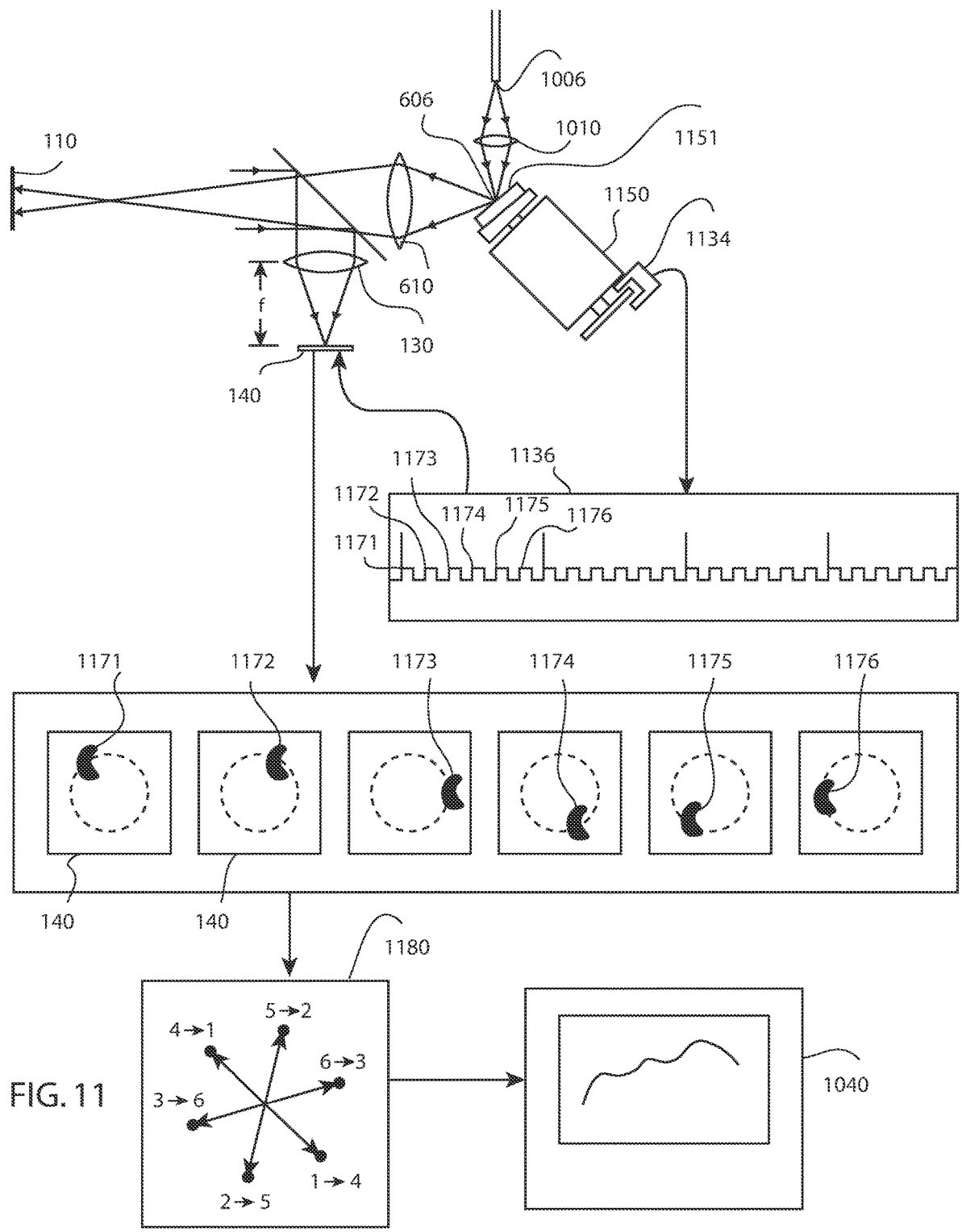

SURFACE SENSING PROBE AND METHODS OF USE

CROSS-REFERENCE TO RELATED APPLICATIONS

This application is a Continuation of U.S. patent application Ser. No. 16/357,263; U.S. Pat. App. Ser. No. 16/357,263 is a Continuation application of U.S. patent application Ser. No. 15/420,555 filed on Jan. 31, 2017; U.S. patent application Ser. No. 15/420,555 is a Continuation application of U.S. patent application Ser. No. 14/281,255 filed on May 19, 2014 now U.S. Pat. No. 9,582,883 issued Feb. 28, 2017; U.S. patent application Ser. No. 14/281,255 is a Continuation-in-Part of U.S. patent application Ser. No. 13/568,229 filed on Aug. 7, 2012 now U.S. Pat. No. 8,761,494 issued Jun. 24, 2014; U.S. patent application Ser. No. 14/281,255 is also a Continuation-in-Part application of U.S. patent application Ser. No. 13/189,349 filed on Jul. 22, 2011 now U.S. Pat. No. 8,736,847 issued May 27, 2014; U.S. patent application Ser. No. 13/189,349 claims benefit of U.S. Pat. App. No. 61/367,409 filed Jul. 24, 2010 and U.S. Pat. App. No. 61/435,283 filed on Jan. 22, 2011; U.S. patent application Ser. No. 14/281,255 is also a Continuation-in-Part application of U.S. patent application Ser. No. 12/921,185 having a 371(c) date of Sep. 7, 2010 now U.S. Pat. No. 8,810,800 issued Aug. 19, 2014; U.S. patent application Ser. No. 12/921,185 is a 371 of PCT App. No. PCT/US09/37,999 filed Mar. 23, 2009; PCT App. No. PCT/US09/37,999 claims benefit of U.S. Pat. App. No. 61/070,352 filed Mar. 22, 2008 and U.S. Pat. App. No. 61/115,923 filed on Nov. 18, 2008; and all of said applications are herein incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND

This invention relates to the sensing of properties of a surface, more particularly, embodiments of the present invention relate to the precision measurement of the location, orientation, and motion of surfaces and to the formation of three-dimensional images and dimensional data of complex objects.

BRIEF SUMMARY OF THE INVENTION

It is an object of one embodiment of the present invention to provide a surface sensing apparatus having at least one source of coherent radiation capable of outputting at least one wavelength emission to create a first illumination state and to illuminate a surface to create a first speckle pattern, an emission deviation facility capable of influencing the emission to illuminate the surface to create a second illumination state and a second speckle pattern, and at least one sensor capable of sensing a representation of the first and a second speckle intensity from the first and second speckle pattern.

It is another object of one embodiment of the present invention to provide the surface sensing apparatus further comprising a waist creating assembly capable of influencing the emission to create at least one illumination waist location and the emission deviation facility is further capable of influencing the at least one illumination waist location to create the first and second speckle pattern.

It is a further object of one embodiment of the present invention to provide the surface sensing apparatus wherein the emission deviation facility further comprises the at least one source of coherent radiation being capable of emitting a first and a second wavelength emission to create a first and second illumination state and create the first and second speckle pattern.

It is yet another object of one embodiment of the present invention to provide the surface sensing apparatus wherein the emission deviation facility further comprises a waist offset creating assembly capable of creating a waist offset and changing the waist offset to create the first and second speckle pattern.

It is another object of one embodiment of the present invention to provide the surface sensing apparatus wherein the emission deviation facility further comprises a waist offset creating assembly capable of creating a waist offset and changing the waist offset to create the first and second speckle pattern and a deflector assembly capable of altering a direction of the illumination state. In some embodiments of the present invention, the emission deviation facility further comprises a waist range offset assembly capable of creating a waist range offset and changing the waist range offset to create the first and second speckle pattern.

It is yet another object of one embodiment of the present invention to provide the surface sensing apparatus further comprising a processor in communication with a memory and the at least one sensor, the processor capable of receiving a representation of the first and second speckle pattern, and the memory containing machine instructions capable of determining a speckle shift from the speckle patterns whereby the processor can calculate at least one system parameter.

It is an object of one embodiment of the present invention to provide a surface sensing apparatus, having at least one source of coherent radiation capable of outputting at least one wavelength emission to illuminate a surface, a relative position of the surface and the emission being variable to create a first surface state and second surface state, each surface state having a speckle pattern, and at least one sensor capable of sensing a representation of a first and a second speckle intensity from the first and second speckle pattern.

It is another object of embodiments of the present invention to provide the surface sensing apparatus further comprising elements such as, but not limited to, a surface deviation facility capable of varying the relative position of the surface and the emission, a range change assembly capable of varying the relative position of the surface and the emission by a range, or a lateral translation assembly capable of varying the relative position of the surface and the emission by a lateral translation.

It is an object of one embodiment of the present invention to provide a method of sensing properties of a surface, and the method comprising the steps of illuminating a surface with at least one source of coherent radiation emission with a first illumination state, sensing a first speckle intensity from the surface from the first illumination state, influencing the emission to create a second illumination state, sensing a second speckle intensity from the surface from the second illumination state, and determining a speckle shift between the first and second speckle intensity.

It is another object of one embodiment of the present invention to provide the method of sensing properties of a surface further comprising the step of calculating at least one surface parameter using the speckle shift.

It is yet another object of one embodiment of the present invention to provide the method of sensing properties of a surface wherein the first and second illumination state have a first and second waist, the difference between the first and second waist comprising a waist offset, and the step of calculating the at least one surface parameter comprises calculating a surface height using the speckle shift and the waist offset.

It is yet another object of one embodiment of the present invention to provide the method of sensing properties of a surface wherein each illumination state having a direction and the difference between the first and second illumination direction is an illumination direction offset, and the step of calculating the surface height further comprises using the speckle shift, the waist offset and the illumination direction offset.

It is another object of one embodiment of the present invention to provide the method of sensing properties of a surface wherein the step of illuminating the surface with at least one source of coherent radiation comprises at least two emissions, each emission having a unique wavelength, the difference between each wavelength is a wavelength change, and the step of calculating the system parameters comprises calculating a surface orientation of the surface using the speckle shift and the wavelength change.

It is an object of one embodiment of the present invention to provide a method of sensing properties of a surface, the method comprising the steps of illuminating a surface with at least one source of coherent radiation emission, the surface having a first surface state, sensing a first speckle intensity from the surface at the first surface state, influencing a relationship of the surface to the emission to create a second surface state, sensing a second speckle intensity from the surface at the second surface state, and determining a speckle shift between the first and second surface state.

It is another object of one embodiment of the present invention to provide the method of sensing properties of a surface further comprising calculating at least one surface parameter using the speckle shift.

It is a further object of one embodiment of the present invention to provide the method of sensing properties of a surface wherein the step of calculating surface parameters further comprises utilizing a processor in communication with a memory and the at least one sensor, the processor receiving a representation of the first and second speckle pattern, and the processor determining a speckle shift from the speckle patterns utilizing the memory containing machine instructions capable of determining a speckle shift from the speckle patterns and at least one system parameter.

It is yet another object of one embodiment of the present invention to provide the method of sensing properties of a surface further comprising the step of illuminating the surface with at least one source of coherent radiation emission being performed at a first surface range, the step of influencing the relationship of the surface to the emission to create a second surface state comprises moving the relationship of the surface and the emission to create a second surface range, and calculating a first surface height and a surface orientation using the speckle shift.

It is still another object of one embodiment of the present invention to provide the method of sensing properties of a surface wherein the step of illuminating the surface with at least one source of coherent radiation emission is performed at a first surface orientation, the step of influencing the relationship of the surface to the emission to create a second surface state comprises moving the relationship of the surface and the emission to create a second surface orientation, and further comprising calculating a change between the first and second surface orientation using the speckle shift.

It is yet another object of one embodiment of the present invention to provide the method of sensing properties of a surface further comprising the step of illuminating the surface with at least one source of coherent radiation emission is performed at a first lateral location, the step of influencing the relationship of the surface to the emission to create a second surface state comprises moving a relationship of the surface and the emission to create a second lateral location, and calculating a change between the first and second lateral location using the speckle shift.

Embodiments of the present invention can be useful as a stand-alone probe, as an element of a measurement system, or as a component of high-speed scanning system. As an example and not for limitation, embodiments of the present invention may find application in areas including industrial inspection, dimensional metrology, assembly, alignment, machine vision, robot vision, and three-dimensional imaging.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A illustrates a coherent radiation source producing an expanding beam emanating from a point and incident on lens; FIG. 6B illustrates an emission deviation facility comprising the additional component of an optical window that may be moved to influence waist range offset; FIG. 6C illustrates an emission deviation facility that achieves a coordinated change of waist offset and illumination direction through a deflector assembly; FIG. 6D illustrates an emission deviation facility that achieves a coordinated change of waist offset and illumination direction by the insertion of a deflector assembly comprised of optical wedge at the plane corresponding to the optical conjugate of plane; FIG. 6E illustrates an emission deviation facility achieves a coordinated change of waist offset and illumination direction by reflecting the illumination beam with a deflector assembly comprised of mirror that tilts; and FIG. 6F illustrates an emission deviation facility that produces a first illumination state with wavelength 1 and a second illumination state with wavelength 2.

FIGS. 7A and 7B are illustrations of additional embodiments of an emission deviation facility Where: FIG. 7A illustrates an emission deviation facility capable of producing illumination state 1 and illumination state 2 by moving the radiation source; and FIG. 7B illustrates an emission deviation facility that produces highly repeatable waist range offsets by sequentially placing optical windows of different thicknesses into the path of the non collimated beam.

FIG. 8A shows an optical receives assembly in relation to an emission deviation facility; FIG. 8B shows an optical receiver comprising a detector placed to receive incoming radiation without passing through other optics; FIG. 8C shows an optical receiver in relation to an emission deviation facility where lens 610 provides the function of lens 130; and FIG. 8D shows a further embodiment of an optical receiver assembly in relation to an emission deviation facility.

FIG. 9A illustrates an embodiment of a detector consisting of a two-dimensional array of closely packed pixels; FIG. 9B illustrates a detector consisting of a linear detector array of closely packed pixels; and FIG. 9C illustrates an embodiment of a detector consisting of at least two separated detectors recording time histories of the speckle intensity at locations separated by the distance D.

FIG. 10A illustrates a measurement system for producing a surface profile of a measurement object; and FIG. 10B illustrates an embodiment where a mirror pivots about the image of a coherent radiation source point.

FIG. 11 is an illustration of one embodiment of a measurement system.

DETAILED DESCRIPTION OF THE INVENTION

Figure 1:
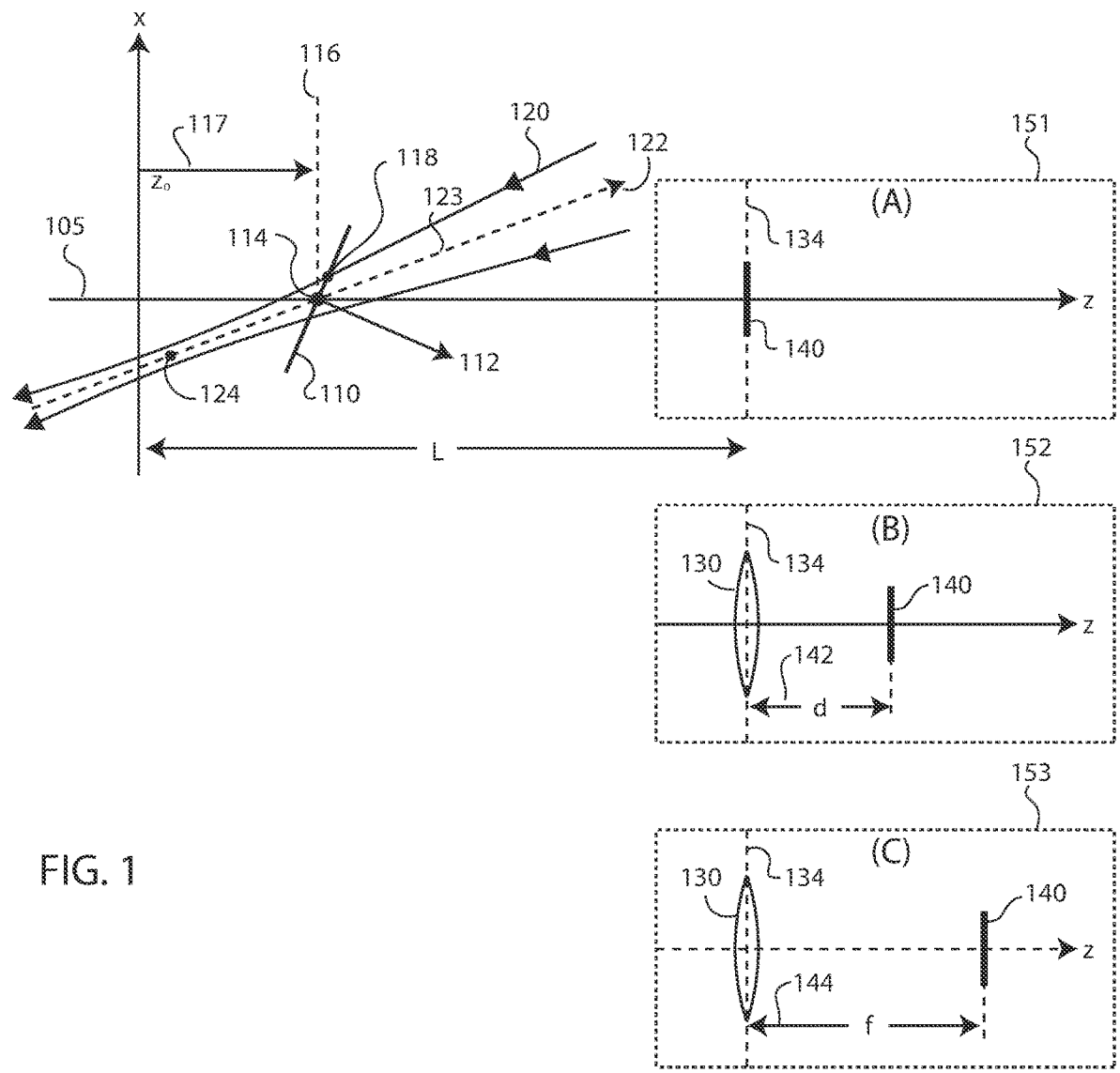
FIG. 1 is a diagram illustrating a system state and sensor modalities for one embodiment of the invention.

A surface sensing system will now be described in detail with reference to the accompanying drawings. It will be appreciated that, while the following description focuses on an optical surface sensing system that probes surface position and orientation at a single surface element, the systems and methods disclosed herein have wide applicability and can be used for the determination of three-dimensional surface shape and object orientation of complex objects. For example, the surface sensing system described herein may be readily employed as a scanning system to rapidly determine dimensions, geometry, location, and orientation of a wide range of objects having surfaces that scatter radiation. The methods are not limited to the optical wavelength range and apply generally to electromagnetic and acoustic waves. The invention provides the capability of performing high-precision measurements at low cost without the shadowing and surface-access issues inherent in triangulation-based approaches. For example, the narrow illumination beam utilized in this invention allows for the measurement of high-aspect-ratio features of an object such as deep holes. In addition, the invention provides for enhanced range resolution and precision compared with time-of-flight approaches that measure the transit time of radiation scattered from the surface of an object. The invention applies to a wide range of measurement scales ranging from microscopic applications to laser-radar applications. Notwithstanding the specific example embodiments set forth below, all such variations and modifications that would be envisioned by one of ordinary skill in the art are intended to fall within the scope of this disclosure.

The phemonology utilized by this invention is described with reference to FIG. 1, which shows surface element 110 in relation to Cartesian coordinate system 105. Surface element 110 intersects the z axis at location 114 lying on plane 116 having z coordinate 117. The direction of surface normal unit vector 112 is denoted in coordinate system 105 through spherical-polar angles $(\theta_s, \phi_s)$ as $$s = i \sin \theta_s \cos \phi_s + j \sin \theta_s \sin \cos \phi_s + k \cos \theta_s. \quad (1)$$

The height profile of surface element 110 is represented by $$z_s = z_0 + \alpha x + \beta y, \quad (2)$$

where $$\alpha = -\tan \theta_s \cos \phi_s$$

$$\beta = -\tan \theta_s \sin \phi_s \quad (3)$$

Coherent illumination beam 120 with wavelength A and beam axis 123 propagates in the direction opposite to unit vector 122 as denoted in coordinate system 105 through spherical-polar angles $(\theta_b, \phi_b)$ as $$b = i \sin \theta_b \cos \phi_b + j \sin \theta_b \sin \cos \phi_b + k \cos \theta_b. \quad (4)$$

In one embodiment, coherent illumination beam 120 is substantially a Gaussian laser beam. Other beam types, however, may also be utilized and will exhibit the same general behavior as described by the following theoretical analysis of Gaussian beams. Coherent illumination beam 120 has a beam waist located at waist position 124. The complex amplitude of a Gaussian beam propagating along the negative $\zeta$ axis of a Cartesian coordinate system $(\xi, \eta, \zeta)$ with waist position 124 located at the origin of coordinate system $(\xi, \eta, \zeta)$ is represented by $$v(\xi, \eta, \zeta) = \frac{A_0}{1 - i\zeta/z_r} \exp\left[-i\frac{\pi}{\lambda}\left(\frac{\xi^2 + \eta^2}{\zeta + iz_r} + 2\zeta\right)\right], \quad (5)$$

where the Rayleigh range $z_r$ is related to the $1/e^2$ intensity radius $w_0$ at waist position 124 by $$z_r = \pi w_0^2 / \lambda, \quad (6)$$

and the beam intensity profile is expressed as $$I = |v_0|^2 \exp[-2(\xi^2 + \eta^2)/w^2], \quad (7)$$

where w is the $1/e^2$ intensity radius point $\zeta$ along the beam axis, which is given by $$w = w_0 \sqrt{1 + \zeta^2/z_r^2}. \quad (8)$$

Within the paraxial approximation, the beam waist radius and the Rayleigh range are related to the f/# that represents the convergence rate of the beam by $$w_0 = \frac{2}{\pi} \lambda f/\# \quad (9)$$

and $$z_r = \frac{4}{\pi} \lambda f/\#^2. \quad (10)$$

The complex amplitude impinging on surface point 118 lying on surface element 110 at lateral coordinates (x, y) is obtained through the coordinate transformation, $$\begin{pmatrix} \xi \\ \eta \\ \zeta \end{pmatrix} = \begin{pmatrix} \cos\theta_b\cos\phi_b & \cos\theta_b\sin\phi_b & -\sin\theta_b \\ -\sin\phi_b & \cos\phi_b & 0 \\ \sin\theta_b\cos\phi_b & \sin\theta_b\sin\phi_b & \cos\theta_b \end{pmatrix} \begin{pmatrix} x - x_b \\ y - y_b \\ z_s(x,y) - z_b \end{pmatrix} \quad (11)$$

that transforms the coordinate system in which the Gaussian beam is defined in Eq. (5) into coordinate system 105. Calculation of the quantity $$\rho^2 = \xi^2 + \eta^2 \quad (12)$$

using Eq. (11) yields $$\rho^2 = [(x-x_b)\sin\phi_b - (y-y_b)\cos\phi_b]^2 + [(x-x_b)\cos\phi_b\cos\theta_b + (y-y_b)\cos\theta_b\sin\phi_b - (z_0-z_b+\alpha x+\beta y)\sin\theta_b]^2 \quad (13)$$

Likewise $$\zeta = (x-x_b)\sin\theta_b\cos\phi_b + (y-y_b)\sin\theta_b\sin\phi_b + (z_0-z_b+\alpha x+\beta y)\cos\theta_b \quad (14)$$

Substitution of Eqs. (13) and (14) into Eq. (5) yields the complex amplitude of the Gaussian beam that impinges on the arbitrary surface point 118 lying on surface element 110:

$$v_P(x, y) = \frac{A_0}{1 - i\zeta/z_r}\exp\left[-i\frac{\pi}{\lambda}\left(\frac{\rho^2}{\zeta + iz_r} + 2\zeta\right)\right]. \quad (15)$$

The scattered complex amplitude $v_P^+(x, y)$ emanating from point 118 is represented by multiplication of the incident complex amplitude at surface point 118 by the complex function g (x, y):

$$v_P^+(x,y) = v_P(x,y)g(x,y). \quad (16)$$

The complex function g (x, y) represents the phase change and reflection loss introduced by scattering from surface point 118. Fresnel propagation of $v_P^+(x, y)$ to plane 134, located at z=L, yields $$v_L(x, y) = \quad (17)$$
$$\int_{-\infty}^{\infty}\int_{-\infty}^{\infty} v_P(x', y')g(x', y')h(x-x', y-y'; L - z_s(x'+y'))dx'dy',$$

where $$h(x, y; z) = \frac{1}{i\lambda z}\exp\left[i\frac{2\pi}{\lambda}\left(z + \frac{x^2+y^2}{2z}\right)\right] \quad (18)$$

is the Fresnel propagation kernel.

In FIG. 1 option (A) 151, detector 140 is placed at plane 134 to detect the speckle intensity at plane 134. The intensity is found by taking the magnitude squared of the complex amplitude, which yields $$I_L(x, y) = \frac{1}{\lambda^2}\left|\int_{-\infty}^{\infty}\int_{-\infty}^{\infty} g(x', y')v_P(x', y')\exp[i\phi_L(x', y')]/ (L - z_0 - \alpha x' - \beta y')dx'dy'\right|^2, \quad (19)$$

where $$\phi_L(x', y') = -\frac{2\pi}{\lambda}(\alpha x' + \beta y') + \frac{\pi}{\lambda}\frac{(x-x')^2 + (y-y')^2}{L - z_0 - \alpha x' - \beta y'}. \quad (20)$$

In FIG. 1 option (B) 152 and option (C) 153, detector 140 is placed at distance d 142 behind plane 134. In option (C) 153, distance d 142 is the focal length f 144 of lens 130. Within the Fresnel approximation, the complex amplitude leaving the lens is the product of the complex amplitude $v_L$ arriving at plane 134 and the complex quadratic phase function representing the transmission function of lens 130 having focal length f 144. The complex amplitude at distance d 142 to the right of lens 130 is obtained by Fresnel propagation over the distance d 142:

$$v_d(x, y) = \int_{-\infty}^{\infty}\int_{-\infty}^{\infty} v_L(x', y')\exp\left[-i\pi\frac{x'^2+y'^2}{\lambda f}\right]h(x-x', y-y'; d)) dx'dy'. \quad (21)$$

The resulting intensity at detector 140 is $$I_d(x, y) = \quad (22)$$
$$\frac{1}{\lambda^2 d^2}\left|\int_{-\infty}^{\infty}\int_{-\infty}^{\infty} g(x', y')v_P(x', y')\exp[i\phi_d(x', y')]/Q(x', y')dx', dy'\right|^2,$$

where $$Q(x', y') = 1 + \left(\frac{1}{d} - \frac{1}{f}\right)(L - z_0 - \alpha x' - \beta y'), \quad (23)$$

and $$\phi_d(x', y') = -\frac{2\pi}{\lambda}\left[\alpha x' + \beta y' + \frac{xx' + yy'}{Q(x', y')d} + \frac{(x'^2+y'^2)(d-f) + (x^2+y^2)(L-f-z_0-\alpha x'-\beta y')}{2Q(x', y')fd}\right]. \quad (24)$$

Note that for option (C) 153 that Q reduces to unity so that Eqs. (22)-(24) take on a particularly simple form with the phase term being reduced to a linear function of x' and y'. Option (C) 153 shows one embodiment where detector 140 is at the Fourier transform plane of lens 130. Equations (19)-(20) and (22)-(24) with the additional equations they reference embody the phenomenology which is exploited in the invention.

Figure 2:
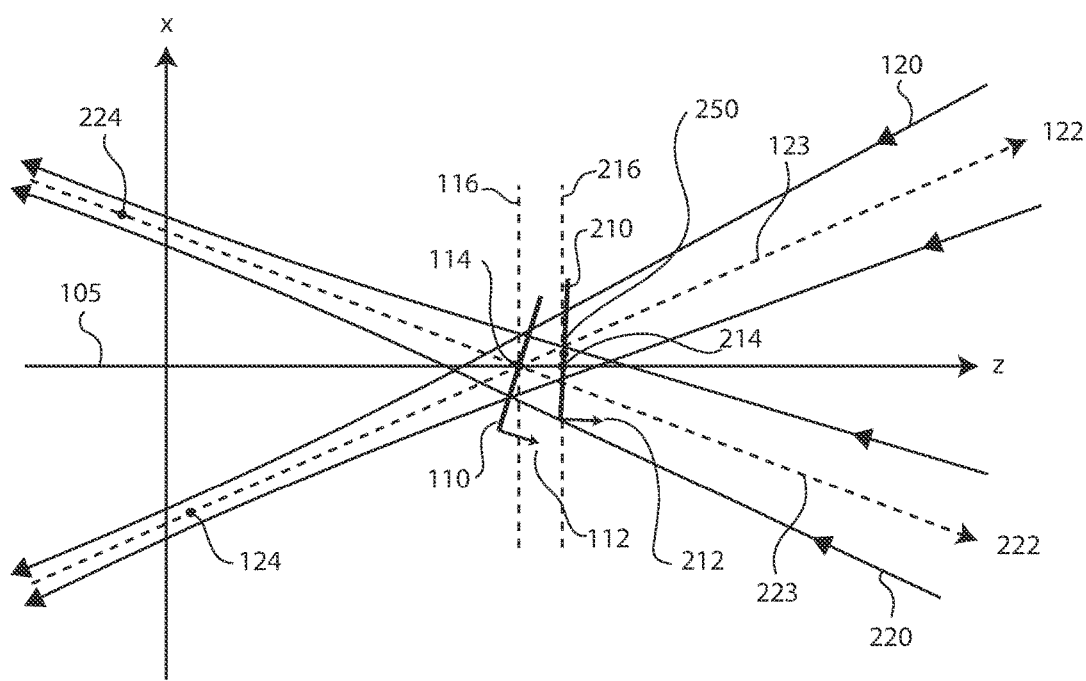
FIG. 2 is a diagram illustrating two system states for one embodiment of the invention.

FIG. 2 describes two system states. System state 1 is comprised of illumination state 1 and surface state 1. System state 2 is comprised of illumination state 2 and surface state 2. As used throughout this description, an illumination state is defined as the properties or parameters of an emission of coherent radiation as they illuminate a surface. Examples of these properties or parameters include but are not limited to the direction of illumination, lateral position of the emission beam waist, offset range of the emission beam waist, the wavelength of the emission/illumination beam and other properties as shown in Table 1. As used throughout this description, a surface state is defined as the properties or parameters of a surface or object. Examples of these properties or parameters include but are not limited to the position and orientation of the surface being sensed, including lateral translations and other properties as shown in Table 1. As used throughout this description, an emission is one or more wavelengths of coherent radiation emitted from a coherent radiation source such as but not limited to a laser.

Examples of illumination states and emissions are also described in U.S. Patent Publication No. US20080154524A1 entitled "METHOD AND APPARATUS FOR REMOTE SENSING OF OBJECTS UTILIZING RADIATION SPECKLE" which is herein incorporated by reference in its entirety.

Generally, and not for limitation, parameters associated with the two system states in FIG. 2 are described in Table 1.

TABLE 1

| | Parameter Name | State 1 | State 2 |
|---|---|---|---|
| Illumination | Wavelength | $\lambda 1$ | $\lambda 2$ |
| | Direction | $(\theta_{b1}, \phi_{b1})$ | $(\theta_{b2}, \phi_{b2})$ |
| | Waist offset | $(x_{b1}, y_{b1},)$ | $(x_{b2}, y_{b2},)$ |
| | Waist range offset | $z_{b1}$ | $z_{b2}$ |
| Surface | Height | $z_{01}$ | $z_{02}$ |
| | Lateral translation | $(0, 0)$ | $(\Delta x, \Delta y)$ |
| | Orientation | $(\alpha_1, \beta_1)$ or $(\theta_{s1}, \phi_{s1})$ | $(\alpha_2, \beta_2)$ or $(\theta_{s2}, \phi_{s2})$ |
| | Orientation change | $(0, 0)$ | $(\Delta\alpha, \Delta\beta)$ |
| Speckle intensity | Location of tracked speckle | $(x_1, y_1)$ | $(x_2, y_2)$ |
| | Speckle shift | $(0, 0)$ | $(s_x, s_y)$ |

Illumination state 1 is represented by coherent illumination beam 120 propagating along beam axis 123 in the direction opposite to unit vector 122. Coherent illumination beam 120 has beam waist position 124 and a first wavelength. Surface state 1 is represented by the location and orientation of surface element 110. Illumination state 2 is represented by coherent illumination beam 220 propagating along beam axis 223 in the direction opposite to unit vector 222. Coherent illumination beam 220 has beam waist position 224 and a second wavelength. Surface state 2 is represented by surface element 110 being translated and rotated into the position represented by repositioned surface element 210. Repositioned surface element 210 has surface normal unit vector 212 and intersects the z axis at intersection location 214 lying on plane 216. Point 250 represents a lateral translation of the center of surface element 110 to the center of repositioned surface element 210. Illumination state 1 and illumination state 2 may be the same or they may comprise parameters that are the same and parameters that are different between state 1 and state 2. For example, wavelength 1 may equal wavelength 2. Likewise, surface state 1 and surface state 2 may be the same or they may have parameters that are the same and parameters that are different between state 1 and state 2. For example, there may be no lateral translation or orientation change between surface state 1 and surface state 2. In addition, there may be no relative motion between surface state 1 and surface state 2 so that repositioned surface element 210 coincides exactly with surface element 110. System state 1 and system state 2 differ when at least one system parameter, represented by illumination parameters and surface parameters in Table 1, differ. Coherent illumination beam 120 and coherent illumination beam 220 may either be derived from the same coherent radiation source, or they may be derived from different coherent radiation sources. It is not necessary for coherent illumination beam 120 and coherent illumination beam 220 to be coherent with respect to each other. System state 1 produces speckle intensity pattern 1 at detector 140. System state 2 produces speckle intensity pattern 2 at detector 140. If coherent illumination beam 1 and coherent illumination beam 2 have a high degree of overlap at surface element 110 and repositioned surface element 210 so that substantially the same scattering cells are illuminated in system state 1 and system state 2, then speckle pattern 1 and speckle pattern 2 are highly correlated. This correlation may manifest itself as speckle pattern 1 and speckle pattern 2 being substantially identical except for a lateral shift in the speckle pattern at the location of detector 140. If a feature in speckle pattern 1 is located at position $(x_1, y_1)$ at the location of detector 140 and this feature moves to position $(x_2, y_2)$ in speckle pattern 2 at the location of detector 140, then the shift in the speckle pattern is denoted by $$s_x = x_2 - x_1$$

$$s_y = y_2 - y_1 \tag{25}$$

Figure 3:
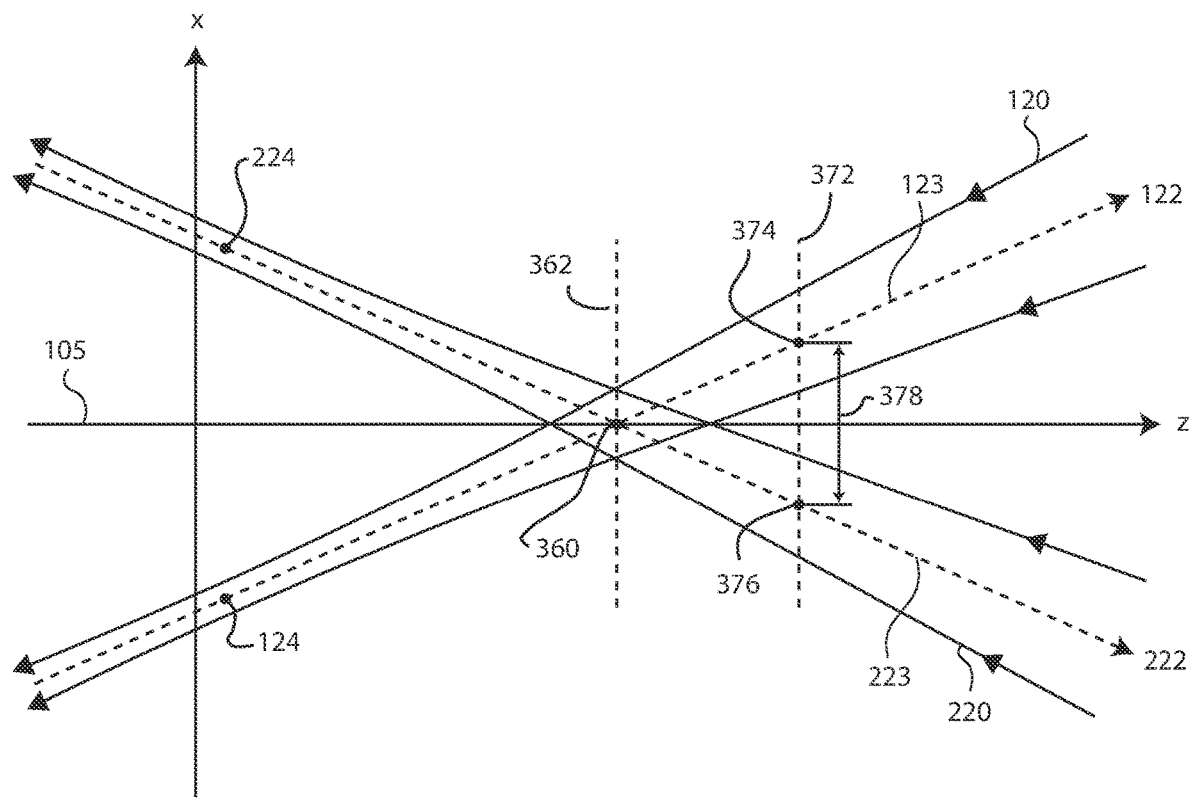
FIG. 3 is a diagram illustrating one embodiment of an overlap between two illumination states.

FIG. 3 describes one embodiment of the invention where beam axis 123 and beam axis 223 intersect at or near the z axis of coordinate system 105. In FIG. 3 the intersection point 360 of beam axis 123 and beam axis 223 lies in plane 362 located at $z = z_c$. Lateral offset 378 is the distance between beam center points 374 and 376 lying on plane 372 located at coordinate z. The condition for beam axis 123 or beam axis 223 to intersect on the z axis at $z = z_c$ is $$x_b + (z_c - z_b) \tan \theta_b \cos \phi_b = 0$$

$$y_b + (z_c - z_b) \tan \theta_b \sin \phi_b = 0 \tag{26}$$

For illumination directions with small angles, $\theta_b \ll 1$, $$x_b + (z_c - z_b) \theta_b \cos \phi_b = 0$$

$$y_b + (z_c - z_b) \theta_b \sin \phi_b = 0 \tag{27}$$

Substantially satisfying Eq. (26) or Eq. (27) for both beam axis 123 and beam axis 223 produces a location in measurement space near $z = z_c$ on the z axis around which measurements are not significantly degraded by decorrelation between speckle pattern 1 and speckle pattern 2. The location of $z_c$ can be chosen to suit the application. A high degree of beam overlap can be achieved during a measurement by coordinating the waist offset and the illumination direction between system state 1 and system state 2 to substantially maintain the relations given by Eq (26) or Eq. (27).

The degree of overlap at the surface is a function of both beam displacement 378 and beam waist w at the surface element. For surface states with equal heights, $z_0 = z_{0_1} = z_{0_2}$, and no lateral translation and for illumination states with symmetric waist offsets and equal waist range offsets $(x_b, y_b, z_b) = (x_{b_2}, y_{b_2}, z_{b_2}) = (-x_{b_1}, -y_{b_1}, z_{b_1})$ and for small angles $\theta_b = \theta_{b_1} = \theta_{b_2} \ll 1$ and azimuth angles related by $\phi_{b_2} - \phi_{b_1} = \pi$, the beam displacement 378 is given by $$\Delta r_c = 2\theta_b |z - z_c| = 2r_b |1 - z/z_c|, \tag{28}$$

where $$r_b = \sqrt{x_b^2 + y_b^2}. \tag{29}$$

The beam waist radius at $z$ is $$w = w_0 \sqrt{1 + (z - z_b)^2 / x_r^2}. \tag{30}$$

An indication of the degree of overlap for surface elements with height $z_0$ is given by $$\gamma = 1 - \frac{\Delta r_c}{2w} = 1 - r_b \frac{|1 - z_0/z_c|}{w_0 \sqrt{1 + (z_0 - z_b)^2 / z_r^2}}. \tag{31}$$

When $\gamma=1$, the beam axes intersect at the surface element and speckle correlation is high. When $\gamma=0$, the $1/e^2$ intensity points of the beams approximately touch, and there is very little beam overlap and a correspondingly low speckle correlation. For fixed $z_c$ there is a range of z values for which $\gamma$ is high enough to provide good measurements. It is possible to achieve high $\gamma$ values over long ranges. For example, if $z_b=0$, $r_b=50$ µm, $z_c=5$ mm, and f/#=10, then $\gamma \geq 0.9$ over the range of 3.3 mm$\leq$z$\leq$10.0 mm. Furthermore, $\gamma \geq 0.8$ for z$\geq$2.5 mm. If $\theta_b=0$ so that there is no beam tilt with respect to the z axis, i.e., $z_c=\infty$, then $\gamma \geq 0.8$ for $|z|\geq 5.0$ mm and $\gamma \geq 0.9$ for $|z|\geq 10.0$ mm. These results for $\gamma$ are insensitive to wavelength and hold from the ultraviolet to the far infrared.

Figure 4:
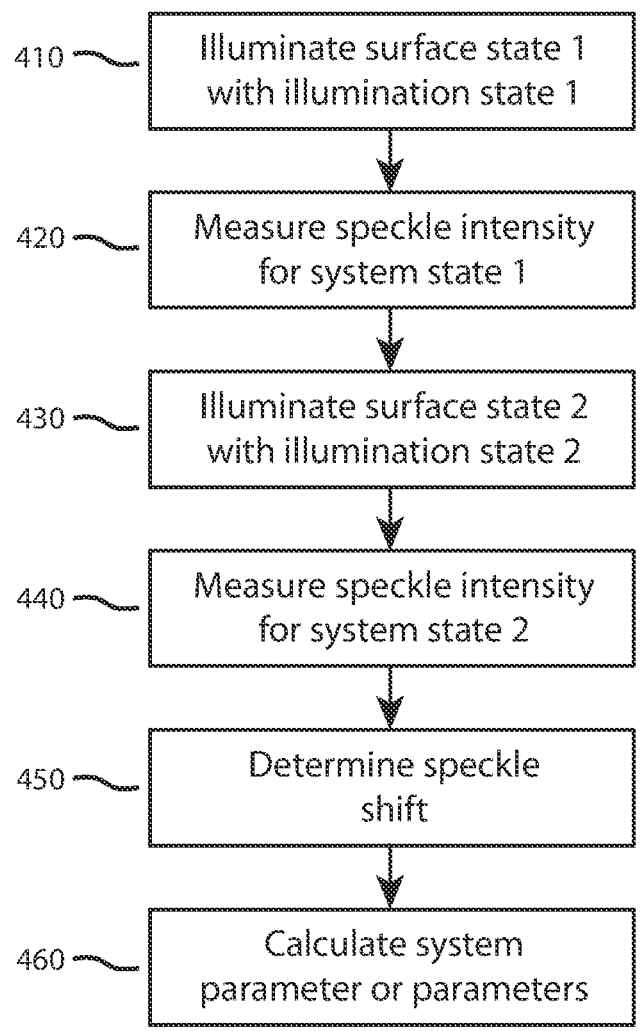
FIG. 4 is a block diagram showing one embodiment of the steps for varying system states and calculating system parameters.

FIG. 4 describes a method for determining a change in at least one system parameter between system state 1 and system state 2 from measurements of the speckle shift resulting from the change between system state 1 and system state 2. In step 410 surface state 1 is illuminated with illumination state 1. In step 420 speckle pattern 1 is measured at at least 1 point. In step 430 surface state 2 is illuminated with illumination state 2. In step 440 speckle pattern 2 is measured at at least 1 point. In step 450, the speckle shift between speckle pattern 1 and speckle pattern 2 is determined. In step 460 at least one system parameter is calculated in response to the change between system state 1 and system state 2.

Measurement of speckle intensity can occur in any of numerous modes. For example, in one embodiment detector 140 is a two-dimensional detector array comprised of at least three detector elements or pixels. Detector element need not lie on a plane. In one embodiment of a two-dimensional detector array the pixels are closely packed and contiguous. In another embodiment detector 140 is a linear array comprised of at least two elements arranged in substantially a straight line. In one embodiment of a linear array, the array is aligned to substantially coincide with the direction of speckle shift. In another embodiment detector 140 is comprised of at least two separated detection elements. In one embodiment of at least two separated detection elements, said detection elements are positioned to be substantially aligned with the direction of speckle shift. In one embodiment of said substantially aligned detector elements, a time history of speckle intensity over a multiple set of system states is produced for each of said detector elements. In one embodiment of said time history, the set of system states is a continuous history produced by a smooth variation of at least one system parameter.

Step 450 of determining the speckle shift can be accomplished through any of many algorithms known by those skilled in the art. For example, speckle shift can be obtained through calculating a cross correlation of two sets of speckle intensity data. The location of the peak of the cross correlation provides the speckle shift. Enhanced precision is achieved through sub-pixel interpolation algorithms. Another example of a method for determining speckle shift is to utilize optical flow algorithms known to those skilled in the art. Yet another method for determining speckle shift is to compare the speckle intensity time histories produced by a set of system states and to determine the time delay associated with features in the speckle pattern to move between detector elements. In one embodiment the determination of speckle shift is performed by a processor in communication with a memory and containing machine instructions capable of determining a speckle shift.

Step 460 of calculating at least one system parameter is performed by relating speckle shift to changes in at least one system parameter through system calibration or through measurement equations derived from the analysis of speckle intensity as related to Eq. (19) or Eq. (22). System calibration may be achieved, for example, by compensating measurement equations for system errors or inaccuracies in the model from which the measurement equations are derived.

A generalized measurement equation is obtained by continuing the analysis that led to Eq. (19) and Eq. (22). Equations (19) and (22) indicate that the speckle pattern intensity can be formulated as the magnitude squared of a Fourier transform. The argument of the Fourier transform contains the spatial coordinates (x, y) of the speckle intensity at detector 140. The speckle shift resulting from transitioning from system state 1 to system state 2 is determined by keeping the arguments of the Fourier transform constant. The argument of the Fourier transform consists of all complex exponential phase terms in Eq. (19) or Eq. (22) that are linear in terms of the variables of integration x' and y'. As long as the remainder of the integrand, excluding g (x', y'), varies slowly with respect to x' and y' and $\gamma$ is high, the integral behaves approximately as the Fourier transform of g, weighted by the magnitude of the incident beam. Consequently, speckle pattern 1 and speckle pattern 2 are highly correlated and related by a simple shift. The behavior of the speckle shift is determined by writing the integrand as a magnitude multiplied by a complex exponential phase component. The phase is then expanded in a power series to obtain an approximation of the linear phase terms.

The phase function $\phi_d$ of Eq. (24) is expanded in a power series as $$\phi_d(x', y') = \phi_{d0} + \phi_{dx} x' + \phi_{dy} y' + \ldots, \quad (32)$$

where $$\phi_{dx} = -\frac{2\pi}{\lambda}\left[\frac{x}{f_d} + \alpha\left(1 - \frac{x^2 + y^2}{2f_d}\right)\right] \quad (33)$$

$$\phi_{dy} = -\frac{2\pi}{\lambda}\left[\frac{y}{f_d} + \beta\left(1 - \frac{x^2 + y^2}{2f_d}\right)\right].$$

and $$f_d = d + (1 - d/f)(L - z_0). \quad (34)$$

The same results are applicable to the expansion of $\phi_L$ of Eq. (20) if we set d=0. Equations (33) and (34) are therefore used in the general case. Option (C) 153 of FIG. 1 reduces to $f_d=f$ and is preferred because the expansion $\phi_d$ in linear terms is exact and because $f_d$ does not depend on the surface height $z_0$.

The complex amplitude incident on point 118 is expressed in terms of a magnitude and a phase component as:

$$v_P(x', y') = |A_0|\frac{z_r}{\sqrt{\zeta^2 + z_r^2}}\exp\left[-\frac{\pi}{\lambda}\left(\frac{\rho^2 z_r}{\zeta^2 + z_r^2}\right)\right]\exp[i\phi_P(x', y')], \quad (35)$$

where $$\phi_P(x', y') = \tan^{-1}\left(\frac{\zeta}{z_r}\right) - \frac{\pi}{\lambda}\frac{\rho^2 \zeta}{\zeta^2 + z_r^2} - \frac{2\pi}{\lambda}\zeta. \quad (36)$$

Expansion(of Eq. (36) in a power series yields $$\phi_P(x', y') = \phi_{P0} + \phi_{Px} x' + \phi_{Py} y' + \ldots, \quad (37)$$

where the linear coefficients are $$\phi_{Px} = \frac{2\pi}{\lambda} \frac{1}{\zeta_0^2 + z_r^2} \left[ -\chi_x \zeta_0 + \frac{\zeta_x}{2} \left( \rho_0^2 \frac{\zeta_0^2 - z_r^c}{\zeta_0^2 + z_r^2} + \frac{\lambda z_r}{\pi} \right) \right] - \frac{2\pi}{\lambda} \zeta_x \quad (38)$$

$$\phi_{Py} = \frac{2\pi}{\lambda} \frac{1}{\zeta_0^2 + z_r^2} \left[ -\chi_y \zeta_0 + \frac{\zeta_y}{2} \left( \rho_0^2 \frac{\zeta_0^2 - z_r^c}{\zeta_0^2 + z_r^2} + \frac{\lambda z_r}{\pi} \right) \right] - \frac{2\pi}{\lambda} \zeta_y,$$

and $$\zeta_0 = (z - z_b)\cos\theta_b - (x_b \cos\phi_b + y_b \sin\phi_b)\sin\theta_b \quad (39)$$

$$\zeta_x = \alpha\cos\theta_b + \sin\theta_b \cos\phi_b$$

$$\zeta_y = \beta\cos\theta_b + \sin\theta_b \sin\phi_b$$

$$\rho_0^2 = (y_b \cos\phi_b - x_b \sin\phi_b)^2 + [(x_b \cos\phi_b + y_b \sin\phi_b)\cos\theta_b + (z - z_b)\sin\theta_b]^2$$

$$\chi_x = -x_b \sin^2\phi_b + y_b \sin\theta_b \sin\phi_b (\alpha\cos\theta_b + \sin\theta_b \cos\phi_b) +$$
$$[(z - z_b)\sin\theta_b + x_b \cos\theta_b \cos\phi_b](\alpha\sin\theta_b - \cos\theta_b \cos\phi_b)$$

$$\chi_y = -y_b \cos^2\phi_b + x_b \sin\theta_b \cos\phi_b (\beta\cos\theta_b + \sin\theta_b \sin\phi_b) +$$
$$[(z - z_b)\sin\theta_b + y_b \cos\theta_b \sin\phi_b](\beta\sin\theta_b - \cos\theta_b \sin\phi_b).$$

In one embodiment, the illumination parameters $\theta_b$, $x_b$, and $y_b$ are small and Eq. (38) reduces to:

$$\phi_{Px} = \frac{2\pi}{\lambda} \left( \frac{x_b(z_0 - z_b) - z_r^2 \theta_b \cos\phi_b + (\alpha + \theta_b \cos\phi_b)\frac{\lambda z_r}{2\pi}}{(z_0 - z_b)^2 + z_r^2} - \alpha \right) \quad (40)$$

$$\phi_{Py} = \frac{2\pi}{\lambda} \left( \frac{x_b(z_0 - z_b) - z_r^2 \theta_b \sin\phi_b + (\beta + \theta_b \sin\phi_b)\frac{\lambda z_r}{2\pi}}{(z_0 - z_b)^2 + z_r^2} - \beta \right).$$

The measurement equation for relating speckle shift to system parameters for a specific operation mode is obtained by requiring that the total combined linear phase remain constant between system state 1 and system state 2:

$$\phi_{Px_1} + \phi_{dx_1} = \phi_{Px_2} + \phi_{dx_2}$$

$$\phi_{Py_1} + \phi_{dy_1} = \phi_{Py_2} + \phi_{dy_2} \quad (41)$$

Figure 5:
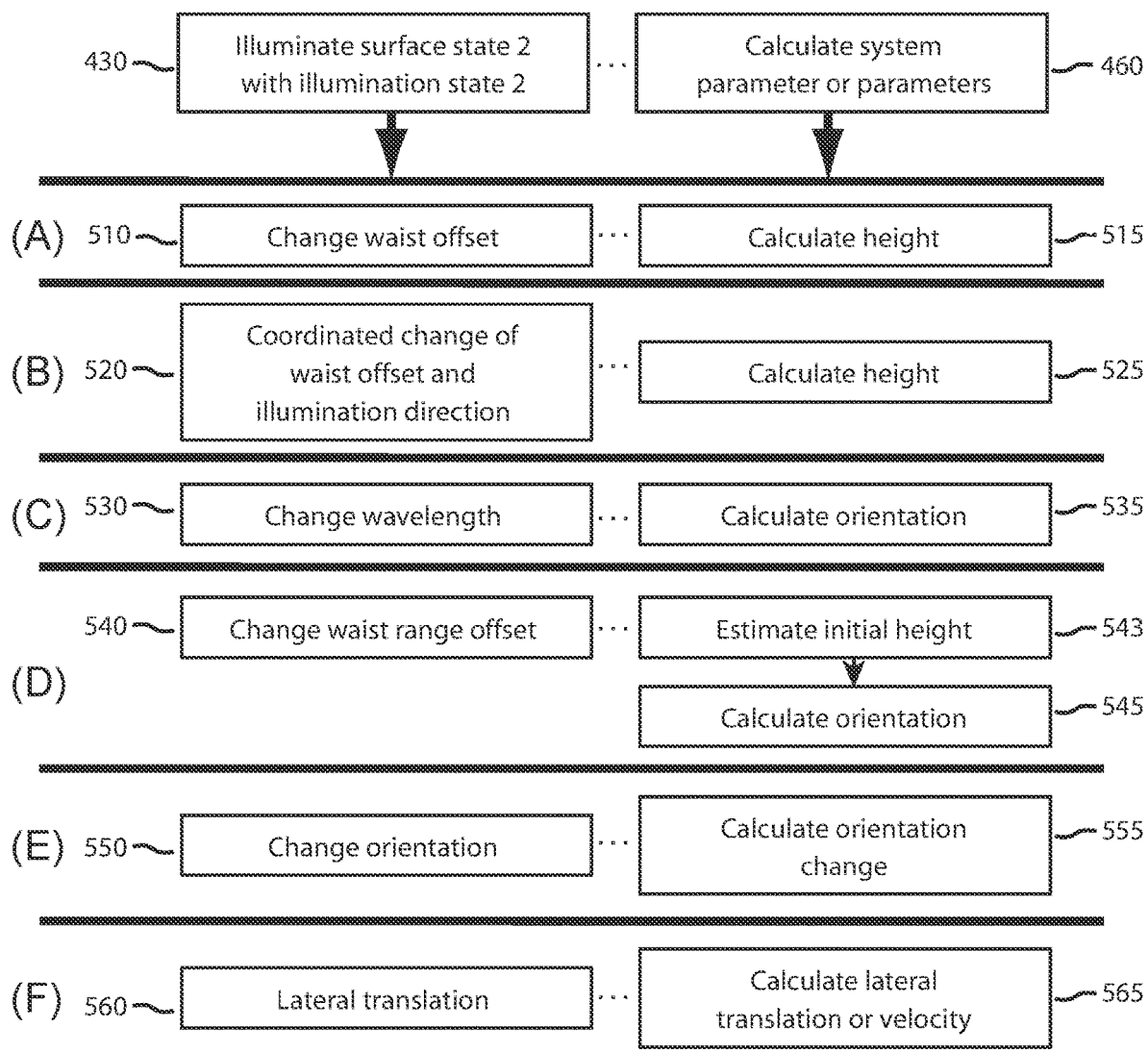
FIG. 5 is a block diagram illustrating example measurement modalities for one embodiment of the invention.

In reference to FIG. 5, six specific operation modes are described in detail. These modes correspond to the specific parameters that are changed in step 430 to achieve system state 2 and to the specific system parameter or parameters are being calculated in step 460. For the purpose of the following illustrative example calculations pertaining to FIG. 5, it is assumed that measurements at detector 140 are symmetric about the origin:

$$(x_2, y_2) = (-x_1, -y_1) = (s_x/2, s_y/2), \quad (42)$$

and unless otherwise stated, that $\theta_b = 0$ and $z_b = 0$. (It is not necessary to number the subscripts when the values of the parameter are the same for both state 1 and state 2.) These assumptions are for illustration only and do not reduce the generality of the results.

In FIG. 5 option (A) step 430 corresponds to the step of changing the waist offset 510 while keeping all other parameters constant. Step 460 corresponds to calculating the height of the surface element. For the purpose of the calculation, let the waist offset be in the x direction and symmetric about the origin:

$$(x_{b_2}, y_{b_2}) = (-x_{b_1}, y_{b_1}) = (b/2, 0), \quad (43)$$

where the total combined waist offset shift between state 1 and state 2 is $$b = x_{b_2} - x_{b_1}. \quad (44)$$

The resulting measurement equation is $$s_x = -bf_d \frac{z_0}{z_0^2 + z_r^2}, \quad (45)$$

which when solved for height yields $$z_0 = -\frac{b(d + \kappa L) \pm \sqrt{b^2(d + \kappa L)^2 - 4s_x(s_x - \kappa b)z_r^2}}{2(s_x - \kappa b)}, \quad (46)$$

where $$\kappa = 1 - d/f. \quad (47)$$

In the embodiment of detection option 153, $\kappa = 0$, and Eq. (46) reduces to $$z_0 = -\frac{bf \pm \sqrt{b^2 f^2 - 4s_x^2 z_r^2}}{2s_x}. \quad (48)$$

When the height is large with respect to the Rayleigh range, $z_r \ll |z_0|$, and Eq. (46) reduces to $$z_0 = -\frac{b(d + \kappa L)}{s_x - \kappa b}. \quad (49)$$

When both conditions $\kappa = 0$ and $z_r \ll |z_0|$ are satisfied, Eq. (46) takes the particularly simple form $$z_0 = -\frac{bf}{s_x}, \quad (50)$$

so that there is an inverse proportionality between height and speckle shift. The relation between height and speckle shift is linear when the magnitude of the height is small with respect to the Rayleigh range $|z_0| \ll z_r$, and $\kappa = 0$:

$$z_0 = -\frac{s_x z_r^2}{bf}. \quad (51)$$

In FIG. 5 option (B), step 430 corresponds to a coordinated change of waist offset and illumination direction 510 and step 460 corresponds to calculation of height 525. In this operation mode, the illumination direction is changed according to Eq. (27) to maintain a high value of γ so that measurement noise due to speckle pattern decorrelation is minimized. Therefore, in this embodiment $\theta_b$ is not assumed to be zero. It is shown explicitly in the equations, but should obey the relation $$\theta_b = -x_b/z_c \quad (52)$$

in order to satisfy Eq. (27) at position $z_c$. The azimuth angles are $\phi_{b_1} = 0$ and $\phi_{b_2} = \pi$ so that Eq. (27) can be satisfied for the waist offset being in the x direction. The measurement equation for option (B) of FIG. 5 is $$s_x = -[d + \kappa(L - z_0)]\frac{bz_0 + \varepsilon}{z_0^2 + z_r^2}, \quad (53)$$

where $$\varepsilon = \theta_b z_r (2z_r - \lambda/\pi). \quad (54)$$

The solution of Eq. (53) for height is:

$$z_0 = -\frac{bd + \kappa(bL - \varepsilon) \pm \sqrt{[bd + \kappa(bL - \varepsilon)]^2 - 4(s_x - \kappa b)[s_x z_r^2 + \varepsilon(d + \kappa L)]}}{2(s_x - \kappa b)}. \quad (55)$$

In detection option 153 of FIG. 1, $\kappa = 0$, and Eq. (55) simplifies to $$z_0 = -\frac{bf \pm \sqrt{b^2 f^2 - 4s_x(s_x z_r^2 + \varepsilon f)}}{2s_x}. \quad (56)$$

In FIG. 5 option (C), step 430 corresponds to a change of wavelength 530 and step 460 corresponds to calculating surface orientation 535. In this operation mode the waist offset is zero in all directions. For a small change $\Delta v$ in optical frequency $v$, the orientation is related to the speckle shift through $$\alpha = -\frac{v}{\Delta v}\frac{s_x}{2f_d}\frac{1}{1 - \frac{s_x^2 + s_y^2}{16 f_d^2} + \frac{\lambda z_r}{4\pi}\frac{z_0^2 - z_r^2}{(z_0^2 + z_r^2)^2}} \quad (57)$$

$$\beta = -\frac{v}{\Delta v}\frac{s_y}{2f_d}\frac{1}{1 - \frac{s_x^2 + s_y^2}{16 f_d^2} + \frac{\lambda z_r}{4\pi}\frac{z_0^2 - z_r^2}{(z_0^2 + z_r^2)^2}}.$$

The azimuth angle of the surface orientation is given simply as $$\phi_s = \tan^{-1}(s_y/s_x). \quad (58)$$

Equation (57) is approximated well by the simplified expression $$\alpha = -\frac{v}{\Delta v}\frac{s_x}{2f_d} \quad (59)$$

$$\beta = -\frac{v}{\Delta v}\frac{s_y}{2f_d}$$

because the second and third terms in the denominator of the third factor are very small with respect to unity.

In FIG. 5 option (D), step 430 corresponds to a change of waist range offset 540 and step 460 corresponds to initially estimating height 543 and calculating surface orientation 545. To illustrate this operation mode, let $z_{b_1} = 0$, $z_{b_2} = \Delta z_b$, and $\kappa = 0$. The surface orientation is related to the speckle shift through $$\alpha = s_x \frac{2\pi}{\lambda f} \frac{z_0^2 + z_r^2}{z_r} \frac{(z_0 - \Delta z_b)^2 + z_r^2}{\Delta z_b(2z_0 - \Delta z_b)} \quad (60)$$

-continued $$\beta = s_y \frac{2\pi}{\lambda f} \frac{z_0^2 + z_r^2}{z_r} \frac{(z_0 - \Delta z_b)^2 + z_r^2}{\Delta z_b(2z_0 - \Delta z_b)}.$$

Since Eq. (60) has a high degree of dependence on the height, $z_0$, an initial estimate of the height is needed to determine the proportionality constant. However, Eq. (58) applies here as well and the azimuth angle of the surface orientation is easily obtained without the necessity of estimating the height. One application of this option is to align a surface perpendicular to a beam. The knowledge of $\phi_s$ provides feedback as to which direction to tilt the surface. The rate of speckle shift provides feedback as to how much additional tilt is required to achieve alignment.

In FIG. 5 option (E), step 430 corresponds to changing the surface orientation 550 and step 460 corresponds to calculating the change in surface orientation 555. This operation mode provides a method for sensing how much an object is tilting and for sensing the dynamics of motion. Let the surface orientation before and after the tilt be given by $$(\alpha_1, \beta_1) = (\alpha, \beta)$$

$$(\alpha_2, \beta_2) = (\alpha + \Delta\alpha, \beta + \Delta\beta) \quad (61)$$

The change in orientation is related to the speckle shift through $$\Delta\alpha = -\frac{s_x}{2f_d}\frac{1}{1 - \frac{s_x^2 + s_y^2}{16 f_d^2} - \frac{\lambda}{4\pi}\frac{z_r}{z_0^2 + z_r^2}} \quad (62)$$

$$\Delta\beta = -\frac{s_y}{2f_d}\frac{1}{1 - \frac{s_x^2 + s_y^2}{16 f_d^2} - \frac{\lambda}{4\pi}\frac{z_r}{z_0^2 + z_r^2}}.$$

These expressions are approximated well by $$\Delta\alpha = -\frac{s_x}{2f_d} \quad (63)$$

$$\Delta\beta = -\frac{s_y}{2f_d}.$$

In FIG. 5 option (F), step 430 corresponds to a relative lateral translation 560 between the illumination beam and the surface and step 460 corresponds to calculating the relative lateral translation 560 or the velocity associated with this translation by taking into account the time between measurement of speckle pattern 1 and speckle pattern 2. The measurement equation associated with option (F) is simply a rearrangement of Eq. (45) for option (A) where $b$ in Eq. (45) is interpreted as $\Delta x$ and the effective waist offset is achieved by motion of the surface rather than changing the waist offset. There is a similar equation for offset in the y direction. Thus $$\Delta x = -s_x \frac{z_0^2 + z_r^2}{f_d z_0} \quad (64)$$

$$\Delta y = -s_y \frac{z_0^2 + z_r^2}{f_d z_0},$$

And both the magnitude and direction of the lateral translation can be determined. The direction of motion is obtained from $$\phi_m = \tan^{-1}(\Delta y/\Delta x) = \tan^{-1}(s_y/s_x) \quad (65)$$

Determination of the magnitude of the lateral translation requires knowledge of the height, which may be known, estimated, or obtained through an auxiliary measurement.

Figure 6A:
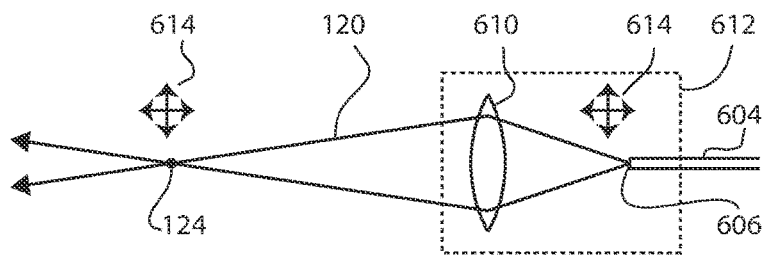
FIGS. 6A-6F are illustrations of multiple embodiments of an emission deviation facility where.
Figure 6B:
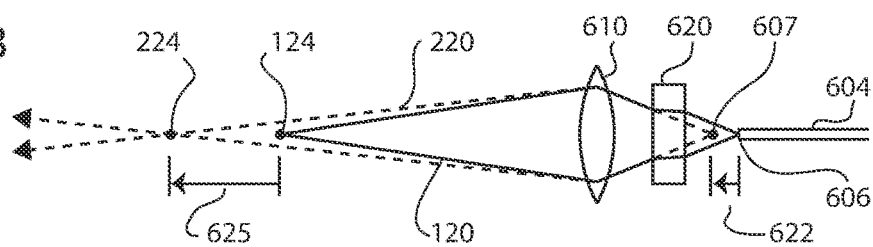
Figure 6C:
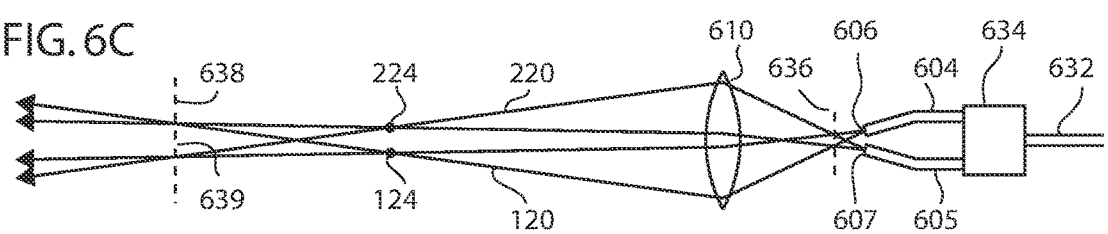
Figure 6D:
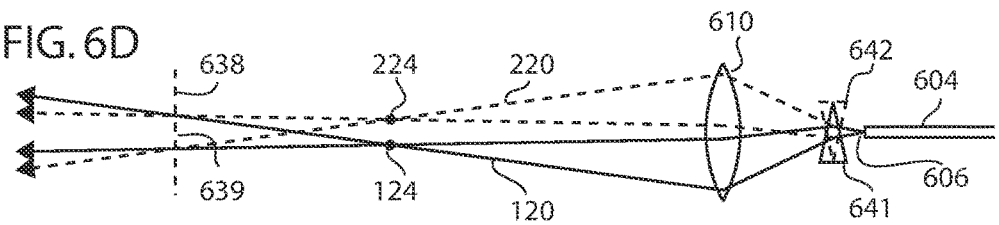
Figure 6E:
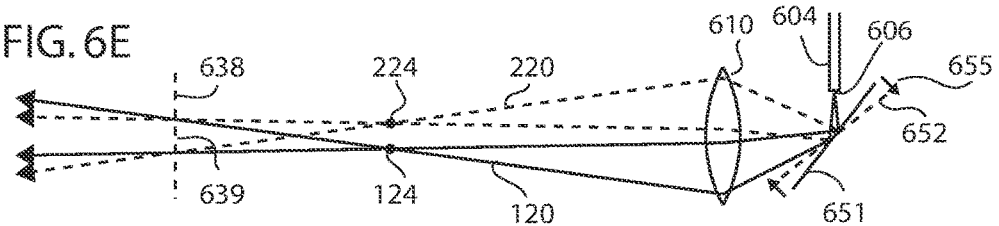
Figure 6F:
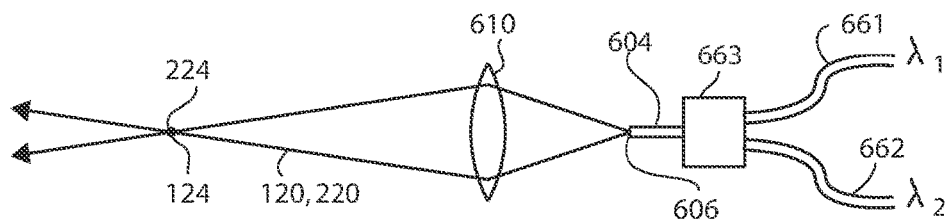

FIGS. 6A-6F describe six embodiments of an emission deviation facility that is capable of producing illumination state 1 and illumination state 2. The emission deviation facility in FIG. 6A comprises a coherent radiation source 604 producing an expanding beam emanating from point 606 and incident on lens 610. In one embodiment coherent radiation source 604 is a laser coupled into a single-mode fiber and point 606 is the tip of the fiber. Assembly 612 holds point 606 and lens 610 in a fixed position relative to each other. Assembly 612 may undergo translation 614 to move waist position 124 to produce illumination states 1 and 2. FIG. 6B is an emission deviation facility comprising the additional component of an optical window 620 that may be moved into the path of the non-collimated laser beam to influence waist range offset 625. FIG. 6C is an emission deviation facility that achieves a coordinated change of waist offset and illumination direction through a deflector assembly to produce region 639 of high beam overlap at plane 638. Plane 638 is the optical conjugate plane of plane 636 where beams emanating from point 606 and point 607 have a high degree of overlap. Coherent radiation sources 604 and 605 may be derived from coherent radiation source 632 through optical switch 634 or they may be derived from different coherent radiation sources not connected to optical switch 634. FIG. 6D is an emission deviation facility that achieves a coordinated change of waist offset and illumination direction by the insertion of a deflector assembly comprised of optical wedge 641 at the plane corresponding to the optical conjugate of plane 638. Optical wedge 641 may rotate about the optical axis to a second position 642 to produce a second illumination state that has a high degree of overlap with illumination state 1. FIG. 6E is an emission deviation facility that achieves a coordinated change of waist offset and illumination direction by reflecting the illumination beam with a deflector assembly comprised of mirror 655 that tilts between position 651 and position 652 to achieve a high degree of beam overlap at plane 638. FIG. 6F is an emission deviation facility that produces a first illumination state with wavelength 1 and a second illumination state with wavelength 2. Coherent radiation source 661 emits radiation at wavelength 1 and coherent radiation source 662 emits radiation at wavelength 2. Combiner 663 combines radiation sources 661 and 662 to produce radiation source 604. Combining may consist of switching between sources or providing both wavelengths simultaneously.

FIG. 7A is an emission deviation facility capable of producing illumination state 1 and illumination state 2 by moving radiation source 604, which produces point 606, to new location 605, which produces point 607. This emission deviation facility may also scan the beam waist to produce measurements at various locations on a surface having multiple surface elements. FIG. 7B is an emission deviation facility that produces highly repeatable waist range offsets 124, 224, and 724 by sequentially placing optical windows 712, 742, and 772 of different thicknesses into the path of the non collimated beam. In one embodiment, windows 124, 224, and 724 are contained in assembly 735 which rotates different windows into place to achieve the desired waist range offset.

It may be desirable to illuminate the object with an illumination spot array that simultaneously illuminates the neighborhoods of multiple locations and to determine the shift between first and second speckle patterns corresponding to each location. One embodiment for producing an illumination spot array is to use a beam replicating element that replicates the beam of coherent radiation at an array of locations. The beam replicating element may be a diffractive optical element beam splitter that replicates the incident beam into multiple directions. If the incident beam is a converging beam, then the multiple directions can form multiple spots.

Figure 8A:
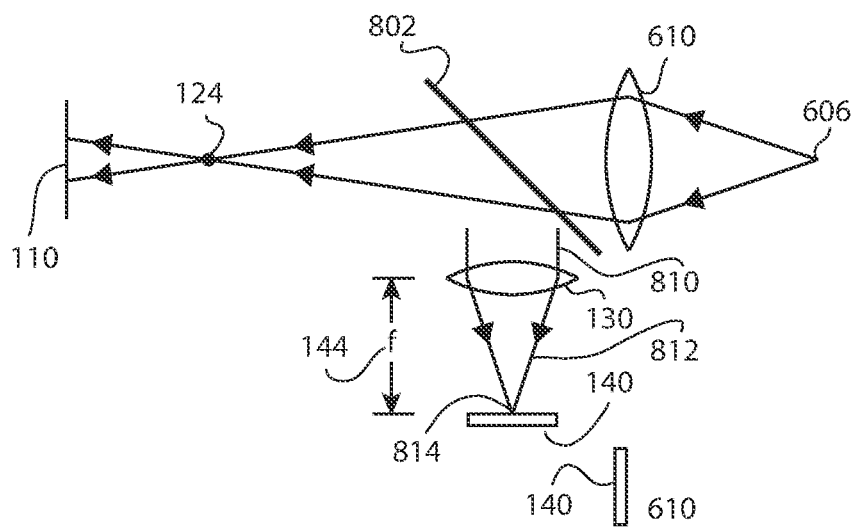
FIGS. 8A-8D is an are illustrations of multiple embodiments of receiver modalities where.
Figure 8B:
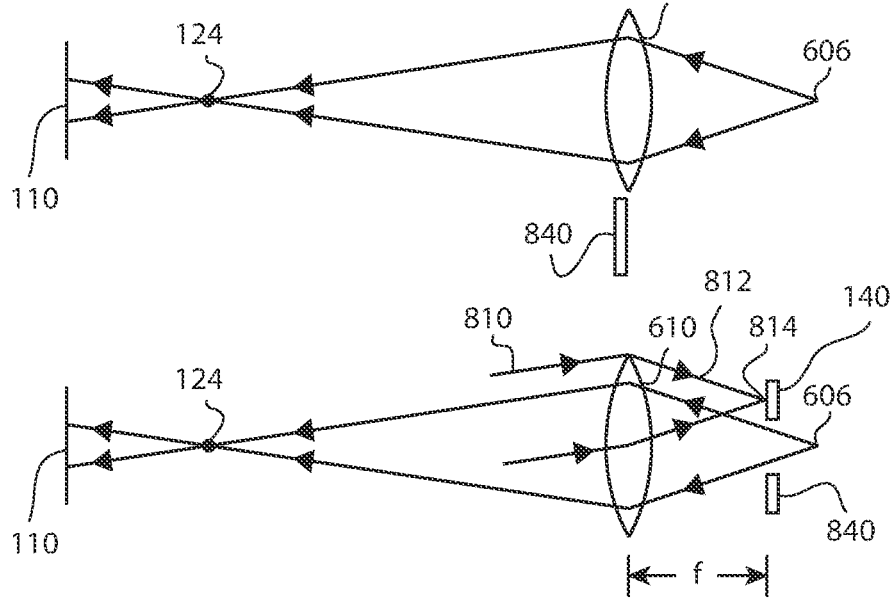
Figure 8C:
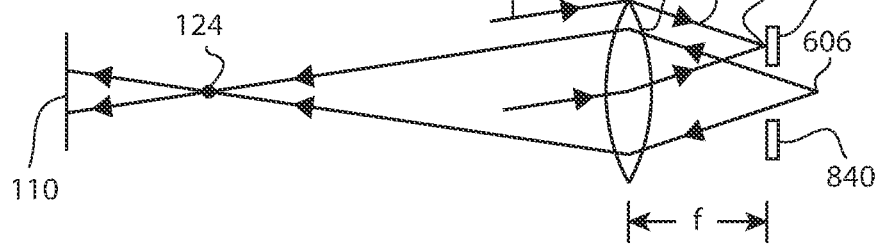
Figure 8D:
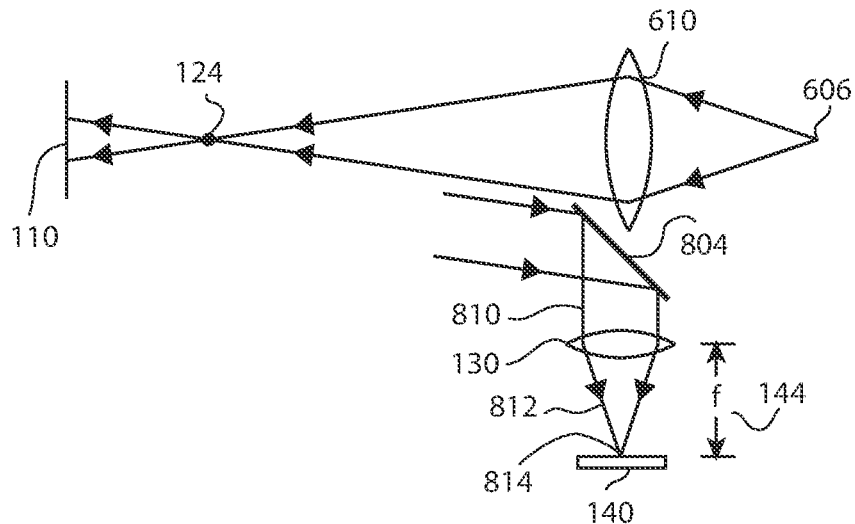

FIG. 8A shows an optical receiver assembly in relation to an emission deviation facility. Beam splitter 802 allows outgoing radiation to pass and reflects incoming radiation into the receiver leg. In the embodiment 153, lens 130 focuses 812 each set of collimated rays 810 of the incoming signal onto single point 814 on detector 140. FIG. 8B shows an optical receiver comprising detector 140 placed to receive incoming radiation without passing through other optics. Optional addition detectors 840 may be placed at various locations around the lens. FIG. 8C shows an optical receiver in relation to an emission deviation facility where lens 610 provides the function of lens 130. In one embodiment detector 140 is located one focal length behind lens 610. Additional detectors 840 may be placed around the outgoing beam emanating from point 606. FIG. 8D shows a further embodiment of an optical receiver assembly in relation to an emission deviation facility. Mirror 804 reflects incoming radiation into lens 130 and detector 140. In one embodiment detector 140 is a focal length f 144 behind lens 130.

Figure 9A:
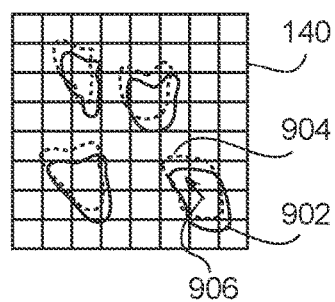
FIGS. 9A-9C are illustrations of multiple detector embodiments where.
Figure 9B:
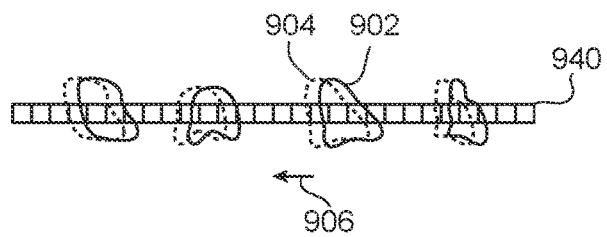
Figure 9C:
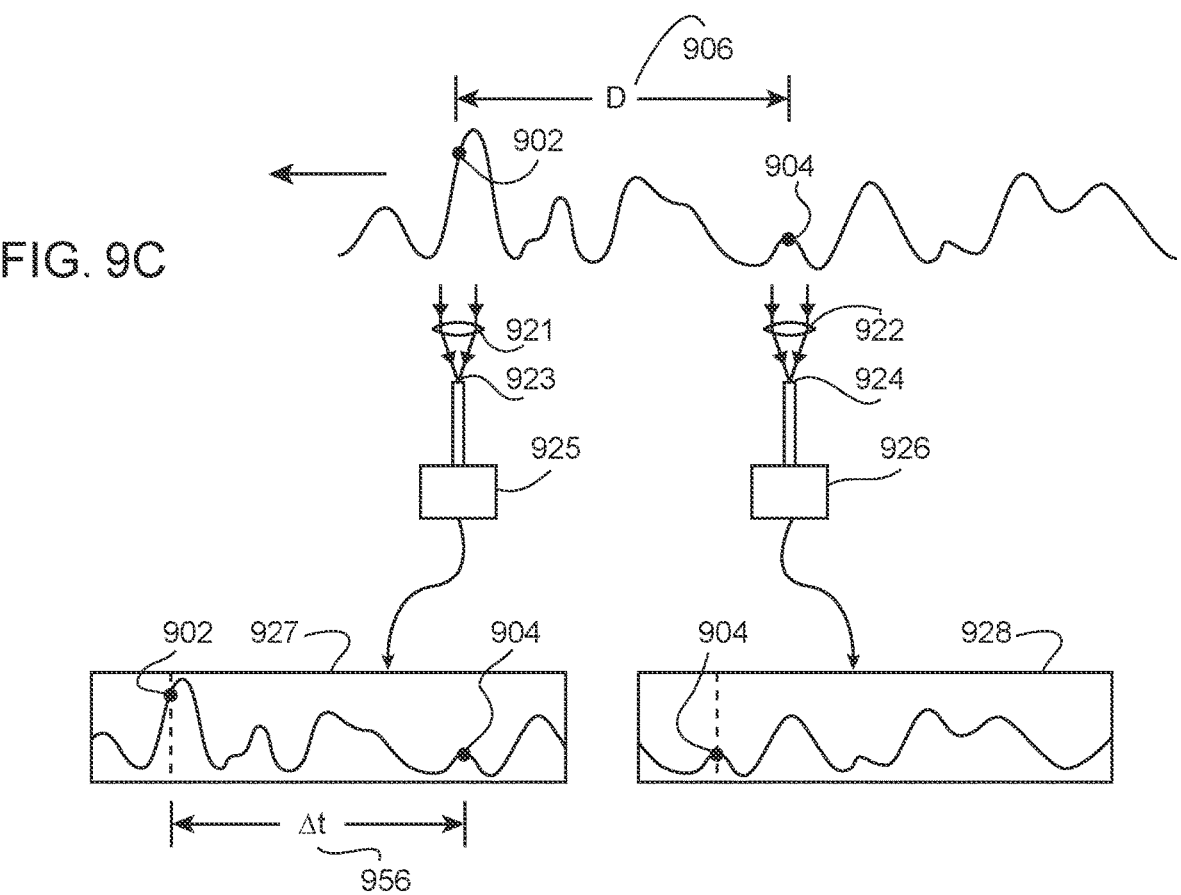

FIG. 9A describes an embodiment of detector 140 consisting of a two-dimensional array of closely packed pixels. Speckle shift 906 corresponds to the shift between feature 902 of speckle pattern 1 and the same feature 904 of speckle pattern 2. FIG. 9B shows a detector consisting of a linear detector array 940 of closely packed pixels. Speckle shift 906 lies substantially along the axis of linear detector array 940. FIG. 9C describes an embodiment of detector 140 consisting of at least two separated detectors 925 and 926 recording time histories 927 and 928 of the speckle intensity at locations separated by the distance D 906. Speckle feature 904 detected by detector 926 is observed by detector 925 at a later time $\Delta t$ 956 corresponding to the time for speckle feature 904 to move the distance D between detectors 926 and 925. In one embodiment detector 925 and 926 are fiber coupled through lenses 921 and 922, which focus incoming radiation onto fiber tips 923 and 924.

Figure 10A:
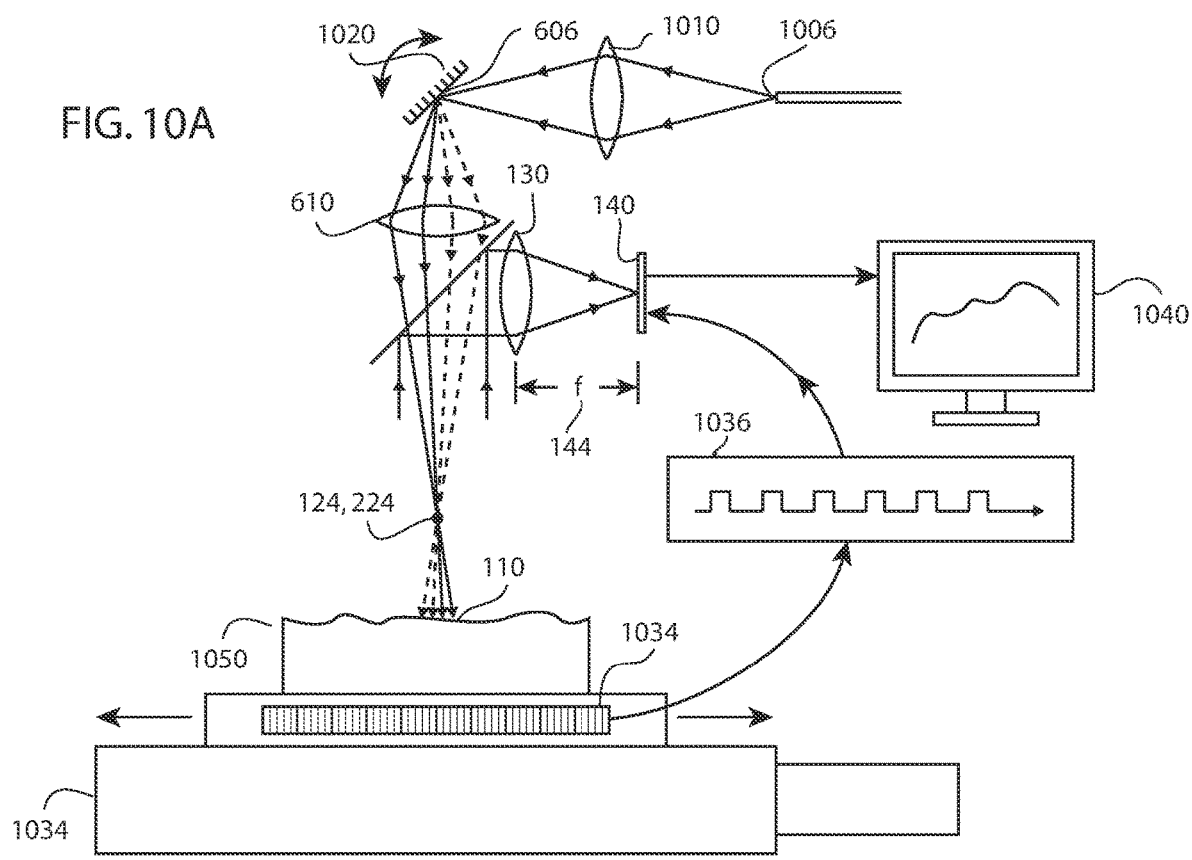
FIGS. 10A-10B are illustrations of one embodiment of a system for measuring surface profiles where.
Figure 10B:
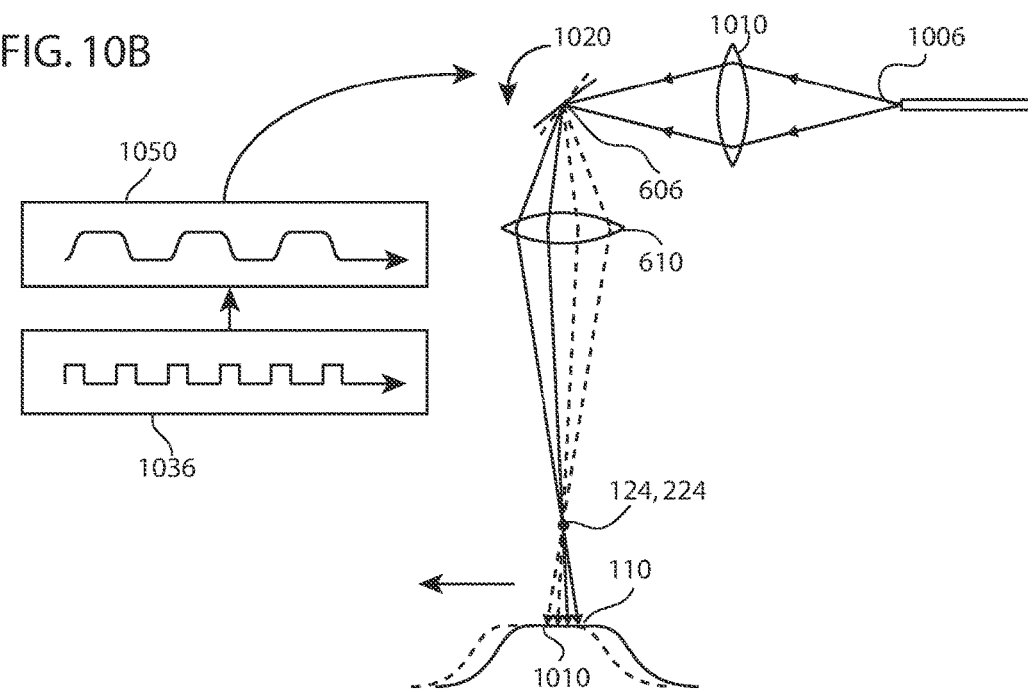

FIG. 10A describes a measurement system for producing a surface profile of measurement object 1050. Coherent radiation source point 1006 is imaged by lens 1010 substantially onto the surface of mirror 1020. Mirror 1020 reflects outgoing radiation into lens 610. Lens 610 produces beam waist 124 in the vicinity of surface element 110. Measurement object 1050 is connected to translation stage 1034, which translates object 1050 laterally. Encoder 1034 produces a pulse train 1036 that triggers detector 140 to take images corresponding to precise increments of translation of object 1050. The effective value of the waist offset b between system state 1 and system state 2 is the known translation increment between measurements as obtained by encoder 1034. The height is measured at each location and the height profile of object 1050 is calculated by processor 1040. In one embodiment, the processor 1040 is a component in a specially programmed computer having the processor in communication with a memory capable of storing and retrieving machine instructions to be executed by the processor. The specially programmed computer being able to communicate the results of executing the machine instructions. In one embodiment detector 140 is located focal length f 144 behind lens 130. In a further embodiment detailed in FIG. 10B, mirror 1020 pivots about the image of coherent radiation source point 1006. A coordinated change of waist offset and illumination direction is achieved at a nominal location $z_c$ by tilting the mirror in response to encoder pulses 1036. The tilt of the mirror oscillates between successive trigger pulses such that illumination state 1 and illumination state 2 produce a coordinated change of waist offset and illumination direction. The amplitude of oscillation can be adjusted to produce an area of high overlap at a desired range of height values.

FIG. 11 describes a measurement system that automatically produces a coordinated change of waist offset and illumination direction based on the concept of FIG. 6E. Motor 1150 spins tilted mirror 1151 such that the beam waist follows a circular trajectory while producing a region of high overlap at a plane that is the optical conjugate of the plane where the focused beam strikes the tilted mirror. Motor 1150 is equipped with rotary encoder 1134. Detector 140 is triggered by encoder pulses 1134 to takes images repeatably at precise points of rotation. In the example of FIG. 11 there are six images per revolution of the mirror. A given speckle feature thus rotates through positions 1171 through 1176 on detector 140. Speckle intensity patterns that occur from pulses that occur at diametrically opposed points of rotation are cross correlated. Cross correlation pattern composite 1180 shows the locations of correlation peaks corresponding to each cross correlation pair. The distance of each cross correlation peak from the center is a measurement of the speckle shift. The magnitude of these speckle shifts is averaged to produce an enhanced measurement. Alternatively, data is only taken at two diametrically opposed locations and processed to form an estimate of the speckle shift. The height value is calculated by processor 1040.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

I claim:

1. A method for determining a translation of a location on an object having a surface, the method comprising:
    illuminating a neighborhood of the location on the object with a source of coherent radiation emission having a beam centerline, a beam direction, and a beam waist thus creating an illumination state and a first speckle pattern;
    sensing the first speckle pattern;
    sensing a second speckle pattern produced by a translation of a position of the location on the object;
    determining the translation of the position of the location on the object in at least two dimensions from the first and second speckle patterns wherein two of the at least two dimensions lie substantially in a plane of the surface of the object;
    wherein the source of coherent radiation emission defines an illumination beam waist;
    wherein the step of determining the translation of the position of the location on the object in at least two dimensions from the first and second speckle patterns depends on a position of the illumination beam waist with respect to the surface of the object;
    wherein the position of the illumination beam waist with respect to the surface of the object defines a scaling factor for converting from a speckle shift to a surface translation; and
    wherein a sign of the scaling factor depends on whether the illumination beam waist is in front of the surface or behind the surface.

2. A method for determining a translation of at least two locations on an object having a surface, the method comprising:
    a source of coherent radiation comprising at least two coherent radiation emissions, each of the at least two coherent radiation emissions having a beam centerline, a beam direction, and a beam waist;
    each of the at least two coherent radiation emissions creating an illumination state and a speckle pattern;
    each of the at least two coherent radiation emissions illuminating a neighborhood of a unique location on the object;
    sensing a first speckle pattern for each of the at least two coherent radiation emissions;
    sensing a second speckle pattern for each of the at least two coherent radiation emissions;
    determining a translation of each of the unique locations on the object in at least two dimensions from the first speckle pattern and the second speckle pattern for each of the at least two coherent radiation emissions wherein two of the at least two dimensions lie substantially in a plane of the surface of the object;
    wherein the at least two coherent radiation emissions each define an illumination beam waist;
    wherein the step of determining a translation of each of the unique locations on the object in at least two dimensions from the first speckle pattern and the second speckle pattern for each of the at least two coherent radiation emissions depends on a position of each of the illumination beam waists with respect to the surface of the object;
    wherein the position of each of the illumination beam waists with respect to the surface of the object defines a scaling factor for converting from a speckle shift to a surface translation for each of the coherent radiation emissions; and
    wherein a sign of each scaling factor depends on whether each of the illumination beam waists are in front of the surface or behind the surface.

3. The method of claim 2, wherein:
    the translation of each of the unique locations on the object comprises a translation of at least one position of at least one of the unique locations on the object; and the translation of at least one position of at least one of the unique locations on the object produces a second speckle pattern for each of the at least two coherent radiation emissions.

4. The method of claim 2, wherein the at least two coherent radiation emissions are produced by a beam replicating element configured to generate a pattern of replicated beams.

5. The method of claim 4, wherein the beam replicating element comprises a diffractive optical element beam splitter.

6. The method of claim 2, wherein the surface comprises a substantially flat surface and the beam direction of each of the at least two coherent radiation emissions are substantially perpendicular to the substantially flat surface.

7. A surface sensing apparatus to determine a translation of a location on an object having a surface, the surface sensing apparatus comprising:
    at least one laser source producing at least one beam of coherent radiation having a centerline, a beam direction, and a beam waist;
    the at least one beam of coherent radiation configured to illuminate a neighborhood of the location on the object;
    a sensor configured to detect a first speckle pattern corresponding to a first surface state and a second speckle pattern corresponding to a second surface state;
    at least one processor in communication with at least one memory element including instructions that when executed cause the processer to calculate a translation of the location on the object in at least two dimensions from the first speckle pattern and the second speckle pattern wherein two of the at least two dimensions lie substantially in a plane of the surface of the object;
    wherein each of the at least one beam of coherent radiation defines an illumination beam waist;
    wherein the instructions that when executed cause the at least one processer to calculate a translation of the location on the object in at least two dimensions from the first speckle pattern and the second speckle pattern depend on a position of the illumination beam waist with respect to the surface of the object;
    wherein the instructions that when executed cause the at least one processer to calculate a translation of the location on the object in at least two dimensions from the first speckle pattern and the second speckle pattern further depend on a scaling factor for converting from a speckle shift to a surface translation; and
    wherein a sign of the scaling factor depends on whether the illumination beam waist is in front of the surface or behind the surface.

8. A surface sensing apparatus to determine a translation of a location on an object having a surface the surface sensing apparatus comprising:
    at least one laser source configured to produce at least one beam of coherent radiation having a centerline, a beam direction, and a beam waist;
    the at least one beam of coherent radiation configured to illuminate a neighborhood of the location on the object;
    a sensor configured to detect a first speckle pattern corresponding to a first surface state and a second speckle pattern corresponding to a second surface state;
    at least one processor in communication with at least one memory element including instructions that when executed cause the processer to calculate a translation of the location on the object in at least two dimensions from the first speckle pattern and the second speckle pattern wherein two of the at least two dimensions lie substantially in a plane of the surface of the object;
    wherein the at least one beam of coherent radiation comprises at least two beams of coherent radiation wherein the at least two beams of coherent radiation are each configured to illuminate the neighborhood of a unique location on the object;
    wherein the sensor being further configured to detect a first speckle pattern and a second speckle pattern for each unique location on the object; and
    wherein the processor further configured to execute the instructions to calculate a translation of each unique location on the object;
    wherein each of the at least one beam of coherent radiation defines an illumination beam waist;
    wherein the instructions executed by the processor to calculate the translation of each unique location on the object depend on a position of each of the illumination beam waists with respect to the surface of the object;
    wherein the instructions executed by the processor to calculate the translation of each unique location on the object depend on a position of each of the illumination beam waists with respect to the surface of the object;
    wherein the instructions executed by the processor to calculate the translation of each unique location on the object apply a scaling factor for converting from a speckle shift to a surface translation for each beam of coherent radiation emission; and
    wherein a sign of each of the scaling factors depends on whether each of the illumination beam waists are in front of the surface or behind the surface.

9. The surface sensing apparatus of claim 8, wherein the at least two beams of coherent radiation are produced by a beam replicating element configured to generate a pattern of replicated beams.

10. The surface sensing apparatus of claim 9, wherein the beam replicating element comprises a diffractive optical element beam splitter.

11. The surface sensing apparatus of claim 10, wherein the surface comprises a substantially flat surface and the beam direction of each of the at least two beams of coherent radiation are substantially perpendicular to the substantially flat surface.

* * * * *